United States Patent [19]

Takaya et al.

[11] Patent Number: 4,598,147

[45] Date of Patent: Jul. 1, 1986

[54] CEPHEM COMPOUNDS AND PROCESSES FOR PREPARATION THEREOF

[75] Inventors: Takao Takaya, Kawanishi; Hisashi Takasugi, Kohamanishi; Toshiyuki Chiba; Kiyoshi Tsuji, both of Osaka, all of Japan

[73] Assignee: Fujisawa Pharmaceutical Co., Ltd., Osaka, Japan

[21] Appl. No.: 676,608

[22] Filed: Dec. 3, 1984

Related U.S. Application Data

[60] Continuation of Ser. No. 421,024, Sep. 22, 1982, abandoned, which is a division of Ser. No. 253,026, Apr. 10, 1981, Pat. No. 4,372,952, which is a division of Ser. No. 59,893, Jul. 23, 1979, Pat. No. 4,284,631.

[30] Foreign Application Priority Data

Jul. 31, 1978 [GB] United Kingdom ............... 31694/78

[51] Int. Cl.$^4$ ............................................. C07D 277/40
[52] U.S. Cl. .................................... 544/238; 544/333; 544/405; 546/280; 548/127; 548/128; 548/131; 548/134; 548/136; 548/143; 548/194
[58] Field of Search ............... 548/194, 127, 128, 131, 548/134, 136, 143; 544/238, 333, 405; 546/280

[56] References Cited

U.S. PATENT DOCUMENTS

| | | | |
|---|---|---|---|
| 4,152,432 | 5/1979 | Heymes et al. | 424/246 |
| 4,278,793 | 7/1981 | Durckheimer | 544/27 |
| 4,288,434 | 9/1981 | Heymes | 424/246 |

*Primary Examiner*—Robert Gerstl
*Attorney, Agent, or Firm*—Oblon, Fisher, Spivak, McClelland & Maier

[57] ABSTRACT

Thiazole intermediates for cephalosporins have been prepared.

7 Claims, No Drawings

CEPHEM COMPOUNDS AND PROCESSES FOR PREPARATION THEREOF

This application is a continuation of Ser. No. 421,024 filed Sept. 22, 1982, now abandoned which is a divisional of Ser. No. 253,026 filed Apr. 10, 1981, now U.S. Pat. No. 4,372,952 which is a divisional of Ser. No. 059,893, filed July 23, 1979, now U.S. Pat. No. 4,284,631.

This invention relates to new cephem compounds. More particularly, it relates to new 7-substituted-3-cephem-4-carboxylic acid, its pharmaceutically acceptable salt and pharmaceutically acceptable bioprecursor thereof, which have antimicrobial activities, and processes for preparation thereof, to intermediate for preparing the same and processes for preparation thereof, and to pharmaceutical composition comprising the same and methods of using the same prophylactically and therapeutically for treatment of infectious diseases in human being and animals.

Accordingly, the objects of this invention are to provide:

new 7-substituted-3-cephem-4-carboxylic acid, its pharmaceutically acceptable salt and pharmaceutically acceptable bioprecursor thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals; and further intermediate to be used for preparation of pharmaceutically active 7-substituted-3-cephem-4-carboxylic acid, its pharmaceutically acceptable salt or pharmaceutically acceptable bioprecursor thereof and methods for preparation of the same.

The cephem compounds of this invention icnlude the compound represented by the formula (I):

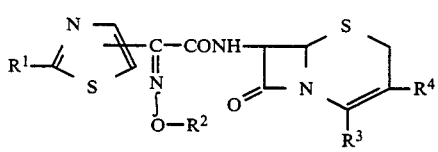

wherein
$R^1$ is amino or protected amino,
$R^2$ is lower alkyl substituted with a substituent selected from the groups consisting of cyano, carbamoyl, hydroxy, protected hydroxy, amino, protected amino, lower alkoxy, lower alkylthio, lower alkenylthio, aryl which may have one or more suitable substituent(s), and heterocyclic group which may have one or more suitable substituent(s),
$R^3$ is carboxy or functionally modified carboxy, and
$R^4$ is hydrogen or halogen, and their pharmaceutically acceptable salts or pharmaceutically acceptable bioprecursors thereof.

The terms and definitions described in this specification are illustrated as follows.

(a) Partial structure of the formula:

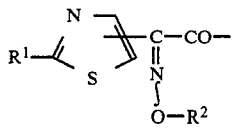

is intended to mean both of the geometric formulae:

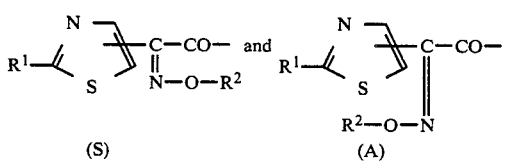

The geometry of the formula (S) is referred to as "syn" and another formula (A) is referred to as "anti".

Accordingly, one isomer of the compound having the partial structure shown by the above formula (S) is referred to as "syn isomer" and another isomer of the compound having the alternative one shown by the above formula (A) is referred to as "anti isomer", respectively.

From the view point of structure-activity relationship, it is to be noted that a syn isomer of the compound (I) tends to be of much higher antimicrobial activity than the corresponding anti isomer, and accordingly the syn isomer of the compound (I) is more preferable antimicrobial agent than the corresponding anti isomer in the prophylactic and therapeutic value.

(b) The thiazolyl group of the formula:

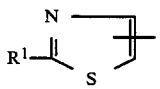

(wherein $R^1$ is as defined above) is well known to lie in tautomeric relation with a thiazolinyl group of the formula:

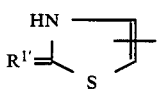

(wherein $R^{1'}$ is imino or protected imino).

The tautomerism between the said thiazolyl and thiazolinyl groups can be illustrated by the following equilibrium:

(wherein $R^1$ and $R^{1'}$ are each as defined above).

Accordingly, it is to be understood that both of the said groups are substantially the same, and the tautomers consiting of such groups are regarded as the same compounds, especially in the manufacturing chemistry. Therefore, both of the tautomeric forms of the compounds having such groups in their molecule are included in the scope of this invention and designated inclusively with one expression "thiazolyl" and represented by the formula:

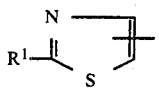

(wherein R¹ is as defined above) only for the convenient sake throughout this specification.

In the above and subsequent descriptions of this specification, suitable examples and illustration of the various definitions which this invention intends to include within the scope thereof are explained in detail as follows.

The term "lower" is used to intend a group having 1 to 6 carbon atom(s), unless otherwise provided.

The term "protective group" in the "protected amino" may include a conventional N-protective group such as acyl, substituted or unsubstituted ar(lower)-alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl for the N-protective group may be aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atoms(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms; lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.); and the like.

The acyl as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), or the like, and preferable example is mono(or di or tri)halo(lower)alkanoyl (e.g., chloroacetyl, dichloroacetyl, trifluoroacetyl, etc.).

And further, the reaction product of a silan, boron, aluminium or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

The term "lower alkyl" may include a residue of straight and branched alkane having 1 to 6 carbon atom(s) such as methyl, ethyl, propyl, isopropyl, butyl, isobutyl, t-butyl, pentyl, neopentyl, hexyl and the like, and preferably the one having 1 to 4 carbon atom(s).

The term "protective group" in the "protected hydroxy" may include a conventional O-protective group such as acyl as aforementioned, or the like.

The term "lower alkoxy" may include straight or branched alkoxy having 1 to 6 carbon atom(s), such as methoxy, ethoxy, propoxy, isopropoxy, utoxy, isobutoxy, tert-butoxy, pentyloxy, isopentyloxy, neopentyloxy, hexyloxy and the like, preferably the one having 1 to 4 carbon atom(s).

The term "lower alkylthio" may include straight and branched alkylthio having 1 to 6 carbon atom(s), such as methylthio, ethylthio, propylthio, isopropylthio, butylthio, isobutylthio, tert-butylthio, pentylthio, neopentylthio, isopentylthio, hexylthio and the like, preferably the one having 1 to 4 carbon atom(s).

The term "lower alkenylthio" may include straight and branched alkenylthio having 2 to 6 carbon atoms, such as vinylthio, allylthio, 1-butenylthio, 2-pentenylthio, 4-pentenylthio, 5-hexenylthio and the like, and preferably the one having 2 to 4 carbon atoms.

The term "aryl" may include a residue of an aromatic hydrocarbon having 6 to 10 carbon atoms, such as phenyl, naphthyl or the like, which may have one or more suitable substituent(s) such as halogen (e.g., chlorine, bromine, iodine or fluorine), nitro, amino, cyano, hydroxy, amino(lower)alkyl (e.g., aminomethyl, aminoethyl, aminopropyl, etc.), protected amino(lower)alkyl as mentioned below, lower alkyl as aforementioned, lower alkoxy as aforementioned, or the like.

The term "heterocyclic group" may include unsaturated 5 to 6-membered heterocyclic group containing at least one hetero atom selected from oxygen, sulfur and nitrogen atoms.

And, preferable heterocyclic group may be the one such as unsaturated 5 to 6-membered heterocyclic group containing 1 to 2 oxygen atom(s), for example, furyl;

unsaturated 5 to 6-membered heterocyclic group containing 1 to 4 nitrogen atom(s), for example, pyrrolyl, imidazolyl, pyrazolyl, pyridyl, picolyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

unsaturated 5 to 6-membered heterocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

unsaturated 5 to 6-membered heterocyclic group containing 1 to 2 sulfur atom(s) and 1 to 3 nitrogen atom(s), for example, thiazolyl, isothiazolyl, thiadiazolyl (e.g., 1,2,4-thiadiazolyl, 1,3,4-thiadiazolyl, 1,2,5-thiadiazolyl, etc.), etc.; and the like;

wherein said heterocyclic group may be substituted with one or more suitable substituent(s) such as lower alkyl is aforementioned, hydroxy, amino, or the like.

More particularly, the preferable example for $R^2$ may be illustrated as follows:

cyano(lower)alkyl (e.g., cyanomethyl, cyanoethyl, cyanopropyl, cyanobutyl, cyanopentyl, etc.);

carbamoyl(lower)alkyl (e.g., carbamoylmethyl, carbamoylethyl, carbamoylpropyl, carbamoylbutyl, carbamoylpentyl, etc.);

hydroxy(lower)alkyl (e.g., hydroxymethyl, hydroxyethyl, hydroxypropyl, hydroxybutyl, hydroxypentyl, etc.);

protected hydroxy(lower)alkyl: lower alkanoyloxy(lower)alkyl (e.g., formyloxymethyl, acetoxymethyl, formyloxyethyl, acetoxyethyl, formyloxypropyl, formyloxybutyl, etc.), benzoyloxy(lower)alkyl (e.g., benzoyloxymethyl, benzoyloxyethyl, benzoyloxypropyl, benzoyloxybutyl, etc.) and the like;

amino(lower)alkyl (e.g., aminomethyl, aminoethyl, aminopropyl, aminobutyl, aminopentyl, etc.);

protected amino(lower)alkyl: lower alkoxycarboxamido(lower)alkyl (e.g., methoxycarboxamidomethyl, ethoxycarboxamidoethyl, propoxycarboxamidomethyl, butoxycarboxamidoethyl, t-butoxycarboxamidomethyl, t-butoxycarboxamidoethyl, t-butoxycarboxamidopropyl, t-butoxycarboxamidohexyl, etc.), and the like;

lower alkoxy(lower)alkyl (e.g., methoxymethyl, methoxyethyl, methoxypropyl, ethoxymethyl, ethoxyethyl, ethoxypropyl, ethoxybutyl, ethoxypentyl, ethoxyhexyl, propoxymethyl, propoxyethyl, propoxypropyl, butoxymethyl, butoxypentyl, pentyloxypentyl, etc.);

lower alkylthio(lower)alkyl (e.g., methylthiomethyl, methylthioethyl, methylthiopropyl, methylthiobutyl, methylthiopentyl, methylthiohexyl, ethylthiomethyl, ethylthioethyl, ethylthiopropyl, propylthioethyl, butylthiopentyl, pentylthiohexyl, etc.);

lower alkenylthio(lower)alkyl (e.g., vinylthiomethyl, allylthiomethyl, 1-propenylthiomethyl, vinylthioethyl, allylthioethyl, 1-propenylthioethyl, butenylthioethyl, pentenylthiopropyl, hexenylthiopentyl, etc.);

phenyl(lower)alkyl (e.g., benzyl, phenethyl, phenylpropyl, phenylbutyl, phenylpentyl, phenylhexyl, xylylmethyl, xylylethyl, benzhydryl, trityl, etc.) which may have 1 to 2 substituent(s) selected from the groups consisting of halogen (e.g., chlorine, bromine, iodine or fluorine), hydroxy, amino(lower)alkyl (e.g., aminomethyl, aminoethyl, aminopropyl, etc.), protected amino(lower)alkyl as aforementioned and lower alkyl (e.g., methyl, ethyl, propyl, butyl, isobutyl, pentyl, hexyl, etc.);

heterocyclic(lower)alkyl: isoxazolyl(lower)alkyl (e.g., 3-isoxazolylmethyl, 3-isoxazolylethyl, etc.), thiazolyl(lower)alkyl (e.g., 4-thiazolylmethyl, 4-thiazolylethyl, etc.) which may have a lower alkyl (e.g., methyl, ethyl, propyl, butyl, isobutyl, pentyl, hexyl, etc.) and the like.

The term "lower alkoxycarboxamido" may include methoxycarboxamido, ethoxycarboxamido, propoxycarboxamido, butoxycarboxamido, t-butoxycarboxamido and the like.

The term "halogen" may include chlorine, iodine, bromine or fluorine.

The term "functionally modified carboxy" may include esterified carboxy, amidated carboxy or the like.

Suitable examples of "the ester" and "ester moiety" in the "esterified carboxy" may be lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxy(lower)alkyl ester (e.g., methoxymethyl ester, ethoxymethyl ester, isopropoxymethyl ester, 1-methoxyethyl ester, 1-ethoxyethyl ester, etc.);

lower alkylthio(lower)alkyl ester (e.g., methylthiomethyl ester, ethylthiomethyl ester, ethylthioethyl ester, isopropylthiomethyl ester, etc.);

halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester, etc.);

ar(lower)alkyl, for example, phenyl(lower)alkyl ester which may have one or more suitable substituent(s) (e.g., benzyl ester, 4-methoxybenzyl ester, 4-nitrobenyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g., phenyl ester, tolyl ester, t-butylphenyl ester, xylyl ester, mesityl ester, cumehyl ester, salicyl ester, etc.); an ester with a silyl compound such as tri(lower)alkylsilyl compound, di(lower)alkylalkoxysilyl compound or tri(lower)alkoxysilyl compound, for example, tri(lower)alkylsilyl ester (e.g., trimethyl silyl ester, triethylsilyl ester, etc.), di(lower)alkylalkoxy silyl ester (e.g., dimethylmethoxysilyl ester, dimethylethoxysilyl ester, diethylmethxysilyl ester, etc.) or tri(lower)alkoxysilyl ester (e.g., trimethxysilyl ester, triethoxysilyl ester, etc.), or the like.

More particularly, the preferable example of ester may be nitrophenyl(lower)alkyl ester (e.g., 4-nitrobenzyl ester, 4-nitrophenethyl ester, lower alkyl ester (e.g., methyl ester, ethyl ester, propyl ester, isopropyl ester, butyl ester, isobutyl ester, tert-butyl ester, pentyl ester, neopentyl ester, hexyl ester, etc.), etc.).

With regard to the terms "protected amino" for $R^1$ and the substituent on the lower alkyl for $R^2$, "protected hydroxy" for the substituent on the lower alkyl for $R^2$ and "functionally modified carboxy" for $R^3$, it is to be understood that these groups bear the meaning not only in synthetic manufacture of the object compound by chemical process(es), but also in physiological and pharmaceutical properties of the object compound per se.

That is, in the meaning of the synthetic manufacture, free amino group for $R^1$ and $R^2$, free hydroxy group for $R^2$ and/or free carboxy group for $R^3$ may be transformed into the "protected amino", "protected hydroxy" and/or "functionally modified carboxy" as mentioned above before conducting the process(es) for preventing any possible undesired side reaction(s), and the "protected amino", "protected hydroxy" and/or "functionally modified carboxy" group in the resultant compound may be transformed into free amino, hydroxy and/or carboxy group after the reaction is conducted. This will be apparent from the explanation of the processes in the following.

On the other hand, in the meaning of the physiological and pharmaceutical properties of the object compound, the compound bearing the "protected amino", "protected hydroxy" and/or "functionally modified carboxy" group is optionally used for improving the properties such as solubility, stability, absorbability, toxicity of the particularly active object compound bearing the free amino, hydroxy and/or carboxy group.

Suitable "pharmaceutically acceptable salt" of the object compound (I) may be conventional nontoxic salt, and may include a salt with an inorganic base or acid, for example, a metal salt such as an alkali metal salt (e.g., sodium salt, potassium salt, etc.) and an alkaline earth metal salt (e.g, calcium salt, magnesium salt, etc.), ammonium salt, an inorganic acid salt (e.g., hydrochloride, hydrobromide, sulfate, phosphate, carbonate, bicarbonate, etc.), a salt with an organic base or acid, for example, an amine salt (e.g., trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g., acetate, maleate, lactate, tartrate, mesylate, benzenesulfonate, tosylate, etc.), a basic or acidic amino acid salt (e.g., arginine salt, aspartic acid salt, glutamic acid salt, lysine salt, serine salt, etc.) and the like.

It is well known in the pharmaceutical field that the active drug, when it has any undesired physiological or pharmaceutical property such as solubility, stability, absorbability, etc., is converted into modified derivative thereof for improving such undesired properties, and then said derivative, upon administration to a patient, exhibits the active efficacy by being converted in the body to the parent drug. In this meaning, the term "pharmaceutically acceptable bioprecursor" used throughout this specification and claim is intended to fundamentally mean all of the modified derivatives, which have structural formulae different from those of the active compounds of this invention, but are converted in the body to the active compounds of this invention upon administration, and also to mean the derivatives which are sometimes derived physiologically from the compounds of this invention in the body and exhibit antimicrobial efficacy.

The compound (I) of this invention can be prepared by the processes as shown in the following scheme.

Process A: N-acylation

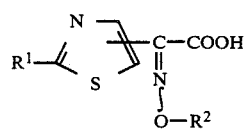
(III)

or its reactive derivative at the carboxy group or a salt thereof

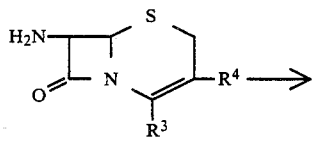

or its reactive derivative at the amino group or a salt thereof

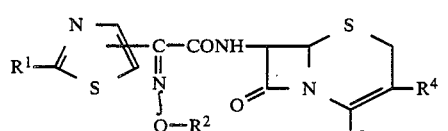

or its salt

Process B: Amidation

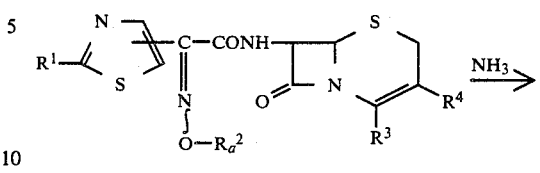
(Ia)

or its salt

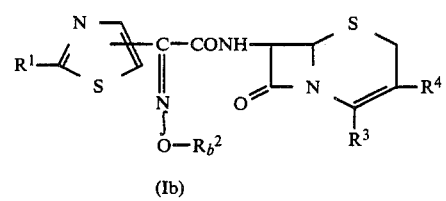
(Ib)

or its salt

Process C: Elimination of amino-protective group

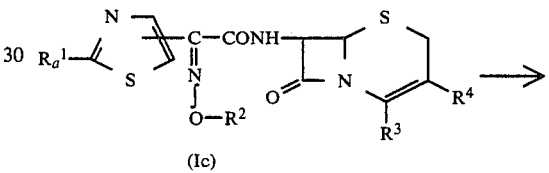
(Ic)

or its salt

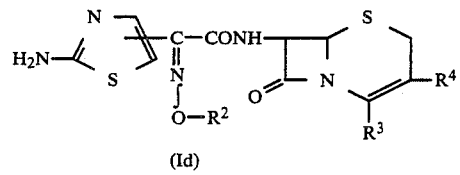
(Id)

or its salt

Process D: Carboxy formation

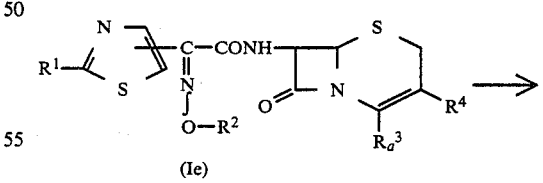
(Ie)

or its salt

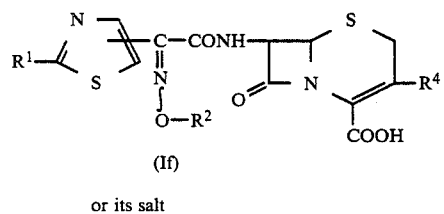
(If)

or its salt

Process E: Elimination of hydroxy-protective group

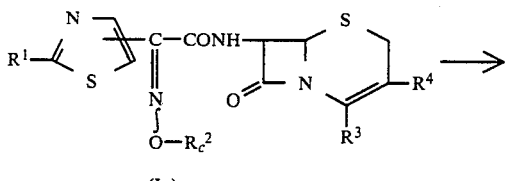

(Ig)

or its salt

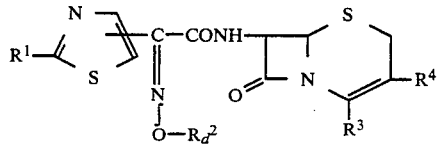

(Ih)

or its salt

Process F: Elimination of amino-protective group

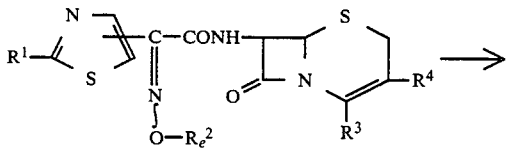

(Ii)

or its salt

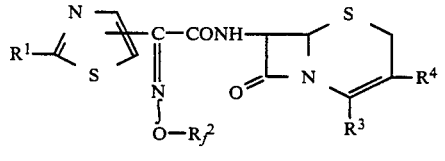

(Ij)

or its salt wherein $R^1$, $R^2$, $R^3$ and $R^4$ are each as defined above, $R_a^1$ is protected amino, $R_a^2$ is lower alkyl substituted with carboxy, $R_b^2$ is lower alkyl substituted with carbamoyl, $R_c^2$ is lower alkyl substituted with protected hydroxy, $R_d^2$ is lower alkyl substituted with hydroxy, $R_e^2$ is lower alkyl substituted with protected amino, $R_f^2$ is lower alkyl substituted with amino, and $R_a^3$ is functionally modified carboxy.

Process A: N-Acylation

The compound (I) or its salt can be prepared by reacting the 7-amino-3-cephem compound (II) or its reactive derivative at the amino or a salt thereof with a carboxylic acid (III) or its reactive derivative at the carboxy or a salt thereof according to a conventional manner of so-called amidation reaction well known in β-lactam chemistry.

The starting compound (III) includes both of known and new ones, and the new compound (III) can be prepared according to the methods as explained hereinafter in this specification.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g., trimethylsilylacetamide, bis(trimethylsilyl)acetamide, etc.), with an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone compound (e.g., acetone, methyl ethyl ketone, methyl isobutyl ketone, acetylacetone, ethyl acetoacetate, etc., or the corresponding ketal, hemiketal or enolate thereof), with phosphorus compound (e.g., phosphorus oxychloride, phosphorous chloride, etc.), or with a sulfur compound (e.g., thionyl chloride, etc.), and the like.

Suitable salt of the compound (II) may be referred to the one as exemplified for the compound (I).

Suitable reactive derivative at the carboxy group of the compound (III) may include, for example, an acid halide, an acid anhydride, an activated amide, an activated ester, and the like, and preferably acid halide such as acid chloride, acid bromide; a mixed acid anhydride with an acid such as substituted phsophoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with imidazole, 4-substituted imidazole, dimethylpyrazole, triazole or tetrazole; an activated ester (e.g., cyanomethyl ester, methoxymethyl ester, dimethylaminomethyl ester, vinyl ester, propargyl ester, 4-nitrophenyl ester, 2,4-dinitrophenyl ester, trichlorophenyl ester, pentachlorophenyl ester, mesylphenyl ester, phenylazophenyl ester, phenyl thioester, 4-nitrophenyl thioester, p-cresyl thioester, carboxymethyl thioester, pyranyl ester, pyridyl ester, piperidyl ester, 8-quinolyl thioester, an ester with an N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Suitable salt of the compound (III) may include a salt with an inorganic base such as alkali metal salt (e.g., sodium salt, potassium salt, etc.) and an alkaline earth metal salt (e.g., calcium salt, magnesium salt, etc.), a salt with an organic base such as tertiary amine (e.g., trimethylamine salt, triethylamine salt, N,N-dimethylaniline salt, pyridine salt, etc.), a salt with an inorganic acid (e.g., hydrochloride, hydrobromide, etc.) and the like.

The suitable reactive derivatives of the compound (II) and (III) can optionally be selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence to the reaction, or an optional mixture thereof.

When the acylating agent (III) is used in a form of free acid or salt in this reaction, the reaction is preferably carried out in the presence of a condensing agent such as a carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g., N,N'-carbonylbis(2-methylimidazole), etc.), an imine compound (e.g., pentamethyleneketene-N-cyclohexylimine, diphenylketene-N-cyclohexylimine, etc.), an olefinic or acetylenic ether compound (e.g., ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g., polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphorus oxychloride (i.e., phosphoryl chloride), phosgene or the like.

With regard to the geometry of the compound (I), it is to be noted that there seems to be stereoselectivity between syn and anti isomers, as explained as follows.

In case that the reaction is conducted by reacting a compound (II) or its reactive derivative at the amino group or a salt thereof with a compound (III) in the presence of a condensing agent, for example, phosphorus pentachloride, thionyl chloride, etc., an anti isomer of the oximino compound (I) tends to be produced as the dominant product and the corresponding syn isomer thereof can hardly be isolated from the reaction product even when a syn isomer of the oximino acylating agent (III) is used. It may be understood that the tendency of such an isomerization in the reaction conducted by the method as explained above is due to the fact that the less stable syn isomer tends to isomerize partially or wholly to the corresponding more stable anti isomer in the course of such reaction, for example, in so-called activation step of the oximino acylating agent (III) so that more stable isomer, i.e., the anti isomer of the oximino compound (I) may be isolated as the reaction product.

Accordingly, in order to obtain a syn isomer of the oximino compound (I) selectively and in high yield, it is preferable to use a syn-isomer of the oximino acylating agent (III), and to conduct the reaction under a selected reaction condition. That is, a syn isomer of the oximino compound (I) can be obtained selectively and in high yield by conducting the reaction of a compound (II) with a syn isomer of the oximino acylating agent (III), for example, in the presence of a Vilsmeier reagent as mentioned above and under around neutral condition.

The object compound (I) and salt thereof are useful as an antimicrobial agent, and a part thereof can also be used as a starting material in the following processes.

In case that the compound (III) wherein $R^2$ is carbamoyl(lower)alkyl is used, the carbamoyl moiety may optionally be dehydrated to the cyano moiety in the pre-treatment, namely; activation of the carboxy group of the compound (III). This case is included within the scope of the present invention.

Process B: Amidation

The compound (Ib) or its salt can be prepared by reacting the compound (Ia) or its salt with ammonia. The present reaction can be carried out in substantially the same manner as that of Process. A. Accordingly, the detailed explanations described in Process A can be referred to the present reaction.

Process C: Elimination of amino-protective group

The compound (Id) or its salt can be prepared by subjecting the compound (Ic) or its salt to elimination reaction of the amino-protective group.

The elimination reaction may be conducted in accordance with a conventional method such as hydrolysis, reduction or the like. These methods may be selected according to the kind of protective group to be eliminated.

The hydrolysis may include a method using an acid (acidic hydrolysis), a base (basic hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like, particulars of which are to be referred to those as illustrated for the N-protective group, respectively.

Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent. Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The hydrolysis using a base can be applied for eliminating the protective group such as an acyl group, preferably, for example, haloalkanoyl (e.g., trifluoroacetyl, etc.) and the like. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as alkali metal acetate (e.g., sodium acetate, potassium acetate, etc.), trialkylamine (e.g., trimethylamine, triethylamine, etc.), alkali metal alkoxide (e.g., sodium methoxide, sodium ethoxide, sodium propoxide, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene, anion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g., trichloroethoxycarbonyl, etc.), substituted or unsubstituted ar(lower)alkoxycarbonyl (e.g., benzyloxycarbonyl, 4-nitrobenzyloxycarbonyl, etc.), 2-pyridylmethoxycarbonyl, aralkyl (e.g., benzyl, benzhydryl, trityl, etc.) and the like. Suitable reduction may include, for example, reduction using an alkali metal borohydride (e.g., sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may optionally be selected in consideration of the chemical property of the starting compound and reaction product as well as the kind of the N-protective group and the method to be applied, and the reaction is preferably carried out under a mild condition such as under cooling, at ambient temperature or slightly elevated temperature.

The process includes in its scope the cases that the protected amino moiety on the lower alkyl for $R^2$ and/or the functionally modified carboxy for $R^3$ is simultaneously transformed into the corresponding free amino group and/or free carboxy group in the course of the above reaction or in the post-treatment.

As to this process, it is to be understood that the purpose of this process lies in providing the generally more active compound (Id) by eliminating the protective group in the protected amino group of the compound (Ic) prepared by the other processes as mentioned above or below.

Process D: Carboxy formation

The compound (If) or its salt can be prepared by transforming the functionally modified carboxy of the compound (Ie) or its salt, into a free carboxy.

This process is to provide a free carboxy compound (If) or its salt, which generally exhibits higher antimicrobial activities as compared with the corresponding functionally modified carboxy compound (Ie) or its salt.

The method to be applied to this process includes conventional ones such as hydrolysis, reduction and the like.

The method of hydrolysis includes a conventional one using an acid, base, enzyme or enzymatic preparation, and the like.

Suitable examples of the acid and base are to be referred to those as exemplified in the above Process C, and the acidic or basic hydrolysis can be carried out in a similar manner to that of the Process C.

Suitable enzyme includes an esterase and esterase preparation which exhibits an esterase activity such as a cultured broth of microorganism or processed materials of broth, the preparation of animal or plant tissues, or the like, and preferably a cultured broth of microorganism or processed material thereof.

An esterase to be used in the enzymatic hydrolysis may be used not only in a purified state, but also in a crude state.

The method of the reduction in this process may be carried out in a similar manner to that of the above Process C.

Process E: Elimination of hydroxy-protective group

The compound (Ih) or its salt can be prepared by subjecting the compound (Ig) or its salt to elimination reaction of the hydroxy-protective group.

The reaction can be carried out in accordance with a conventional method such as hydrolysis, reduction or the like. These methods may be selected according to the kind of the protective group to be eliminated.

The hydrolysis may include a method using an acid (acidic hydrolysis), a base (basic hydrolysis) or hydrazine, and the like, and these methods may be applied to the hydrolysis mentioned in Process C.

The reduction may be also applied to the reduction mentioned in Process C.

The process includes within its scope the cases that the protected amino group for $R^1$ and/or the protected hydroxy moiety on the lower alkyl for $R^2$ is simultaneously transformed into the corresponding free amino group and/or free hydroxy group in the course of the reaction or the post-treatment.

Process F: Elimination of amino-protective group for $R_e^2$

The compound (Ij) or its salt can be prepared by subjecting the compound (Ii) or its salt to elimination reaction of the amino-protective group.

The present reaction can be carried out in substantially the same manner as that of Process C. Accordingly, the detailed explanations described in Process C can be referred to the present reaction.

The compound obtained in accordance with the processes as explained above can be isolated and purified in a conventional manner.

In case that the object compound (I) has free carboxy, hydroxy or amino group in the molecule, it may be transformed into its pharmaceutically acceptable salt by a conventional method.

The object compound (I), its pharmaceutically acceptable salt and bioprecursor thereof exhibit high antimicrobial activities inhibiting the growth of a wide variety of pathogenic microorganisms including Gram-positive and Gram-negative bacteria and are useful as antimicrobial agents.

According to the aforementioned processes, more specifically the following compounds can be prepared.

(1) 7-[2-(2-aminothiazol-4-yl)-2-cyanomethoxyiminoacetamido]-3-cephem-4-carboxylic acid (syn isomer)

(2) 7-[2-(2-formamidothiazol-4-yl)-2-carbamoylmethoxyiminoacetamido]-3-cephem-4-carboxylic acid (syn isomer).

(3) 7-[2-(2-aminothiazol-4-yl)-2-(2-hydroxyethoxyimino)acetamido]-3-cephem-4-carboxylic acid (syn isomer).

(4) 7-[2-(2-aminothiazol-4-yl)-2-(2-ethoxyethoxyimino)acetamido]-3-cephem-4-carboxylic acid (syn isomer).

(5) 7-[2-(2-aminothiazol-4-yl)-2-methylthiomethoxyiminoacetamido]-3-cephem-4-carboxylic acid (syn isomer).
(6) 7-[2-(2-aminothiazol-4-yl)-2-(2-allylthioethoxyimino)acetamido]-3-cephem-4-carboxylic acid (syn isomer).
(7) 7-[2-(2-aminothiazol-4-yl)-2-(2-aminoethoxyimino)acetamido]-3-cephem-4-carboxylic acid dihydrochloride (syn isomer).
(8) 7-[2-(2-formamidothiazol-4-yl)-2-(2-tertbutoxycarboxamidoethoxyimino)-acetamido]-3-cephem-4-carboxylic acid (syn isomer).
(9) 7-[2-(2-aminothiazol-4-yl)-2-benzyloxyiminoacetamido]-3-cephem-4-carboxylic acid (syn isomer).
(10) 7-[2-(2-aminothiazol-4-yl)-2-(3-isoxazolylmethoxyimino)acetamido]-3-cephem-4-carboxylic acid (syn isomer).
(11) 7-[2-(2-formamidothiazol-4-yl)-2-methylthiomethoxyiminoacetamido]-3-cephem-4-carboxylic acid (syn isomer).
(12) 7-[2-(2-formamidothiazol-4-yl)-2-(2-formyloxyethoxyimino)acetamido]-3-cephem-4-carboxylic acid (syn isomer).
(13) 7-[2-(2-formamidothiazol-4-yl)-2-(2-ethoxyethoxyimino)acetamido]-3-cephem-4-carboxylic acid (syn isomer).
(14) 7-[2-(2-formamidothiazol-4-yl)-2-(2-allylthioethoxyimino)acetamido]-3-cephem-4-carboxylic acid (syn isomer).
(15) 7-[2-(2-formamidothiazol-4-yl)-2-cyanomethoxyiminoacetamido]-3-cephem-4-carboxylic acid (syn isomer).
(16) 4-nitrobenzyl 7-[2-(2-aminothiazol-4-yl)-2-benzyloxyiminoacetamido]-3-cephem-4-carboxylate (syn isomer).
(17) 7-[2-(2-formamidothiazol-4-yl)-2-(3-isoxazolylmethoxyimino)acetamido]-3-cephem-4-carboxylic acid (syn isomer).
(18) 4-nitrobenzyl 7-[2-(2-formamidothiazol-4-yl)-2-carbamoylmethoxyiminoacetamido]-3-cephem-4-carboxylate (syn isomer).
(19) 7-[2-(2-formamidothiazol-4-yl)-2-(2-methylthiazol-4-yl)-methoxyiminoacetamido]-3-cephem-4-carboxylic acid (syn isomer).
(20) 7-[2-(2-aminothiazol-4-yl)-2-(2-methylthiazol-4-yl)-methoxyiminoacetamido]-3-cephem-4-carboxylic acid hydrochloride (syn isomer).
(21) 4-nitrobenzyl 7-[2-(2-formamidothiazol-4-yl)-2-(3-tert-butoxycarboxamidopropoxyimino)acetamido]-3-chloro-3-cephem-4-carboxylate (syn isomer).
(22) 7-[2-(2-formamidothiazol-4-yl)-2-(3-tertbutoxycarboxamidopropoxyimino)acetamido]-3-chloro-3-cephem-4-carboxylic acid (syn isomer).
(23) 7-[2-(2-aminothiazol-4-yl)-2-(3-aminopropoxyimino)acetamido]-3-chloro-3-cephem-4-carboxylic acid dihydrochloride (syn isomer).
(24) 4-nitrobenzyl 7-[2-(2-formamidothiazol-4-yl)-2-(2-tert-butoxycarboxamidoethoxyimino)acetamido]-3-chloro-3-cephem-4-carboxylate (syn isomer).
(25) 7-[2-(2-formamidothiazol-4-yl)-2-(2-tertbutoxycarboxamidoethoxyimino)acetamido]-3-chloro-3-cephem-4-carboxylic acid (syn isomer).
(26) 7-[2-(2-aminothiazol-4-yl)-2-(2-aminoethxyimino)acetamido]-3-chloro-3-cephem-4-carboxylic acid dihydrochloride (syn isomer).
(27) 7-[2-(2-formamidothiazol-4-yl)-2-(3-tertbutoxycarboxamidopropoxyimino)acetamido]-3-cephem-4-carboxylic acid (syn isomer).
(28) 7-[2-(2-aminothiazol-4-yl)-2-(3-aminopropoxyimino)acetamido]-3-cephem-4-carboxylic acid (syn isomer).
(29) 7-[2-(2-formamidothiazol-4-yl)-2-(4-bromo-3-hydroxybenzyloxyimino)acetamido]-3-cephem-4-carboxylic acid (syn isomer).
(30) 7-[2-(2-aminothiazol-4-yl)-2-(4-bromo-3-hydroxybenzyloxyimino)acetamido]-3-cephem-4-carboxylic acid (syn isomer).
(31) 7-[2-(2-formamidothiazol-4-yl)-2-(4-tertbutoxycarboxamidobenzyloxyimino)acetamido]-3-cephem-4-carboxylic acid (syn isomer).
(32) 7-[2-(2-aminothiazol-4-yl)-2-(4-aminoethylbenzyloxyimino)acetamido]-3-cephem-4-carboxylic acid dihydrochloride (syn isomer).
(33) 7-[2-[2-(2,2,2-trifluoroacetamido)thiazol-4-yl]-2-(2,4-dichlorobenzyloxyimino)acetamido]-3-cephem-4-carboxylic acid (syn isomer).
(34) 7-[2-(2-aminothiazol-4-yl)-2-(2,4-dichlorobenzyloxyimino)acetamido]-3-cephem-4-carboxylic acid (syn isomer).
(35) 4-nitrobenzyl 7-[2-[2-(2,2,2-trifluoroacetamido)thiazol-4-yl]-2-(4-fluorobenzyloxyimino)acetamido]-3-cephem-4-carboxylate (syn isomer).
(36) 7-[2-[2-(2,2,2-trifluoroacetamido)thiazol-4-yl]-3-(4-fluorobenzyloxyimino)acetamido]-3-cephem-4-carboxylic acid (syn isomer).
(37) 7-[2-(2-aminothiazol-4-yl)-2-(4-fluorobenzyloxyimino)acetamido]-3-cephem-4-carboxylic acid (syn isomer).
(38) 4-nitrobenzyl 7-[2-[2-(2,2,2-trifluoroacetamido)thiazol-4-yl]-2-(4-methylbenzyloxyimino)acetamido]-3-cephem-4-carboxylate (syn isomer).
(39) 7-[2-[2-(2,2,2-trifluoroacetamido)thiazol-4-yl]-2-(4-methylbenzyloxyimino)acetamido]-3-cephem-4-carboxylic acid (syn isomer).
(40) 7-[2-(2-aminothiazol-4-yl)-2-(4-methylbenzyloxyimino)acetamido]-3-cephem-4-carboxylic acid (syn isomer).

In order to show the utility of the active compound (I), the test data of some representative compounds (I) are shown in the following.

1. IN VITRO ANTIBACTERIAL ACTIVITY (1) Test method

In vitro antibacterial activity was determined by the two-fold agar-plate dilution method as described below.

One loopful of the 100-fold dilution of an overnight culture of each test strain in Trypticasesoy broth was streaked on heart infusion agar (HI-agar) containing graded concentrations of the test compound and incubated at 37° C. for 20 hours. The minimal inhibitory concentration (MIC) was expressed in µg/ml.

(2) Test compounds

| No. 1 | 7-[2-(2-aminothiazol-4-yl)-2-cyanomethoxyiminoacetamido]-3-cephem-4-carboxylic acid (syn isomer) |
|---|---|
| No. 2 | 7-[2-(2-aminothiazol-4-yl)-2-(2-hydroxyethoxyimino)acetamido]-3-cephem-4-carboxylic acid (syn isomer) |
| No. 3 | 7-[2-(2-aminothiazol-4-yl)-2-(2-ethoxyethoxyimino)acetamido]-3-cephem-4-carboxylic acid (syn isomer) |
| No. 4 | 7-[2-(2-aminothiazol-4-yl)-2-(methyl- |

-continued

| | thiomethoxyimino)acetamido]-3-cephem-4-carboxylic acid (syn isomer) |
|---|---|
| No. 5 | 7-[2-(2-aminothiazol-4-yl)-2-(4-aminomethylbenzyloxyimino)acetamido]-3-cephem-4-carboxylic acid dihyrochloride (syn isomer) |
| No. 6 | 7-[2-(2-aminothiazol-4-yl)-2-(3-isoxazolylmethoxyimino)acetamido]-3-cephem-4-carboxylic acid (syn isomer) |

(3) Test results

| Test strain | MIC (μg/ml) Compound | | | | | |
|---|---|---|---|---|---|---|
| | 1 | 2 | 3 | 4 | 5 | 6 |
| *Staphylococcus aureus* 209 P JC-1 | 6.25 | 12.5 | 3.13 | 1.56 | 0.78 | 3.13 |
| *Escherichia coli* NIHJ JC-2 | 0.05 | 0.05 | 0.2 | 0.05 | 0.10 | 0.10 |
| *Proteus vulgaris* IAM-1025 | 0.025 | 0.025 | 0.025 | 0.025 | 0.05 | 0.025 |
| *Klebsiella pneumoniae* 20 | 0.025 | 0.025 | 0.025 | 0.025 | 0.05 | 0.025 |
| *Proteus mirabilis* 18 | 0.025 | 0.025 | 0.2 | 0.05 | 0.10 | 0.10 |
| *Pseudomonus aeruginosa* NCTC-10490 | 1.56 | 3.13 | 1.56 | 1.56 | 3.13 | 1.56 |

Some of the starting compound (III) used in Process A are novel and can be represented by the following formula:

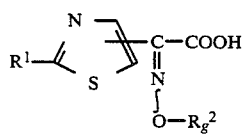

(IIIa)

wherein
R$^1$ is amino or protected amino, and
R$_g^2$ is lower alkyl substituted with a substituent selected from the groups consisting of hydroxy, protected hydroxy, amino, lower alkoxycarboxamido, lower alkoxy, lower alkylthio, lower alkenylthio, aryl which may have one or more suitable substituent(s), and heterocyclic group which may have one or more suitable substituent(s),
and its ester and a salt thereof.

The stating compound (IIIa) can be prepared by the methods illustrated below.

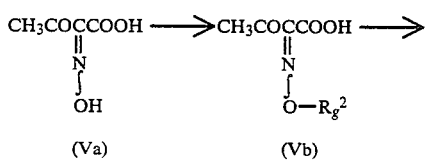

(1)

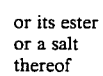

(Va)

or its ester
or a salt
thereof (Vb)

or its ester
or a salt
thereof

-continued

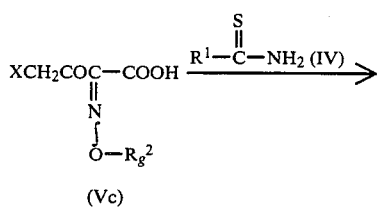

(Vc)

or its ester
or a salt
thereof

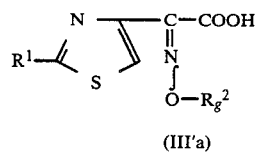

(III'a)

or its ester
or a salt
thereof

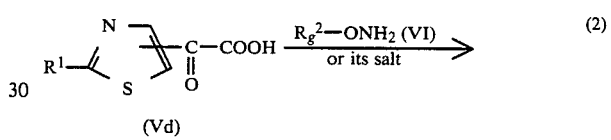

(2)

(Vd)

or its ester or
a salt thereof

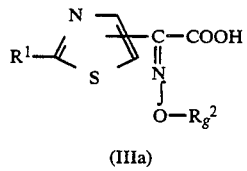

(IIIa)

or its ester or
a salt thereof

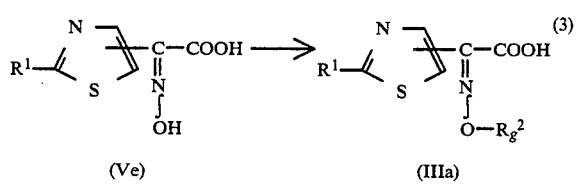

(3)

(Ve)

or its ester or
a salt thereof (IIIa)

or its ester or
a salt thereof

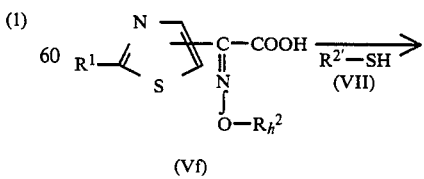

(4)

(Vf)

or its ester or
a salt thereof

-continued

(IIIb)

or its ester or
a salt thereof

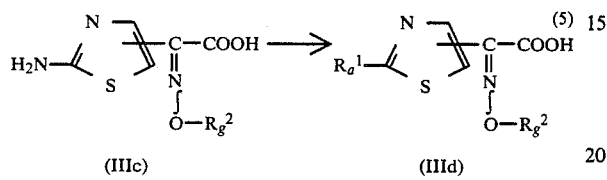

(IIIc) (IIId)

or its ester or         or its ester or
a salt thereof          a salt thereof

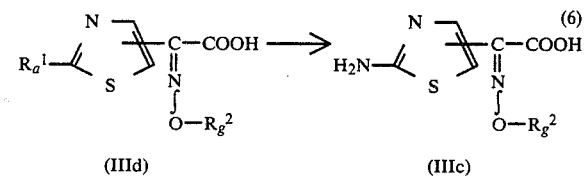

(IIId) (IIIc)

or its ester or         or its ester or
a salt thereof          a salt thereof

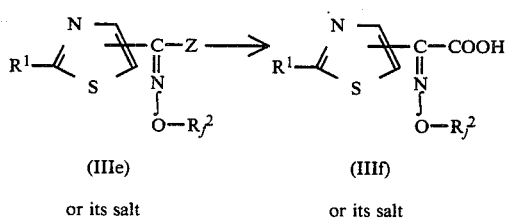

(IIIe) (IIIf)

or its salt             or its salt

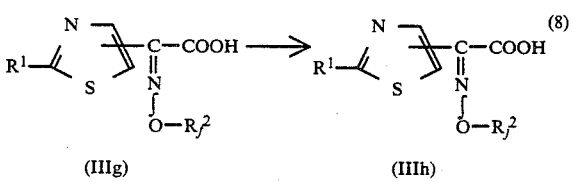

(IIIg) (IIIh)

or its ester or         or its ester or
a salt thereof          a salt thereof

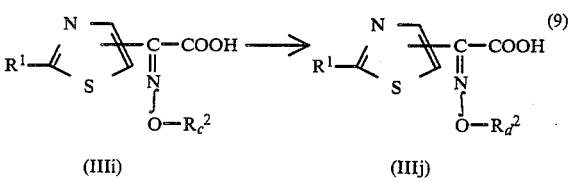

(IIIi) (IIIj)

or its ester or         or its ester or
a salt thereof          a salt thereof

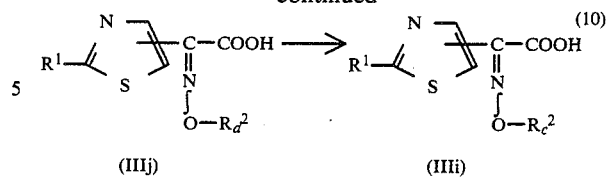

(IIIj) (IIIi)

or its ester or         or its ester or
a salt thereof          a salt thereof wherein
$R^1$, $R_a{}^1$, $R_c{}^2$, $R_d{}^2$, $R_f{}^2$, and $R_g{}^2$ are each as defined above,
$X_2$ is halogen,
$R_h{}^2$ is lower alkyl substituted with halogen,
$R^{2'}$ is lower alkenyl,
$R_i{}^2$ is lower alkyl substituted with lower alkenylthio,
$R_j{}^2$ is lower alkyl substituted with lower alkoxycarboxamido, and
Z is esterified carboxy.

Process 1: Etherification

The compound (Vb) or its ester or a salt thereof, or the compound (IIIa) or its ester or a salt thereof can be prepared by reacting the compound (Va) or its ester or a salt thereof, or the compound (Ve) or its ester or a salt thereof with an etherifying agent, respectively.

The etherifying agent may include a compound of the formula:

$$R_g{}^2-X$$

wherein
$R_g{}^2$ is as defined above, and
X is halogen.

The reaction is usually carried out in a solvent such as water, acetone, ethanol, diethyl ether, dimethylformamide or any other solvent which does not adversely influence the reaction, within a temperature range of cooling to heating, preferably in the presence of a base such as an inorganic or organic base as aforementioned in Process C as illustrated before.

Process 2: Halogenation

The compound (Vc) or its ester or a salt thereof can be prepared by reacting the compound (Vb) or its ester or a salt thereof with a halogenating agent.

The suitable halogenating agent may be halogen (e.g., bromine, chlorine, etc.), sulfuryl halide (e.g., sulfuryl bromide sulfuryl chloride, etc.), N-halosuccinimide (e.g., N-bromosuccinimide, etc.) or the like.

The reaction is usually carried out in a solvent such as acetone, diethyl ether, N,N-dimethylformamide, tetrahydrofuran, ethyl acetate, acetic acid or any other solvent which does not adversely influence the reaction. The reaction temperature is not critical and the reaction may be preferably conducted within a temperature range of cooling to somewhat elevated temperature.

Process 3: Thiazole ring formation

The compound (IIIa') or its ester or a salt thereof can be prepared by reacting the compound (Vc) or its ester or a salt thereof with a thiourea compound (IV).

The reaction is usually conducted in a solvent such as water, alcohol (e.g., methanol, ethanol, etc.), benzene, acetone, N,N-dimethylformamide, tetrahydrofuran, diethyl ether, dioxane or any other solvent which does not adversely influence the reaction.

The reaction temperature is not critical and the reaction may be preferably carried out within a temperature range of ambient temperature to heating.

Process 4: Oximation

The compound (IIIa) or its ester or a salt thereof can be prepared by reacting a compound (Vd) or its ester or a salt thereof with a hydroxyamine derivative of the formula (VI) or its salt. Suitable salt of the hydroxyamine derivative (VI) may be hydrochloride, hydrobromide, sulfate or the like.

The reaction is usually conducted in a conventional solvent such as water, alcohol, tetrahydrofuran, acetonitrile, dimethylsulfoxide, pyridine or any other solvent which does not adversely influence the reaction, or a mixture thereof, and the reaction temperature is not critical, and the reaction is preferably carried out under a mild condition, for example, under cooling to ambient temperature.

In case that a salt of the hydroxylamine derivative (VI) is used as a reagent, the reaction is preferably conducted in the presence of a conventional base as aforementioned in Process C.

Process 5

The compound (IIIb) or its ester or a salt thereof can be prepared by reacting the compound (Vf) or its ester or a salt thereof with lower alkenylmercaptan (VII) such as allylmercaptan, 3-butenylmercaptan, 4-pentenylmercaptan, and the like.

The reaction is usually conducted in a conventional solvent such as water, alcohol, tetrahydrofuran, acetonitrile, dimethylformamide, pyridine, or any other solvent which does not adversely influence the reaction, or a mixture thereof. The reaction temperature is not critical, and the reaction may be preferably carried out under a mild condition such as under cooling or at ambient temperature.

The reaction can be conducted preferably in the presence of a conventional base as aforementioned Process C.

Process 6: Introducing the amino protective group

The compound (IIId) or its ester or a salt thereof can be prepared by reacting the compound (IIIc) or its ester or a salt thereof with the introducing agent of amino protective group.

Suitable introducing agent of amino protective group may include an acylating agent.

The reaction is usually carried out in a solvent such as water, methanol, ethanol, ethyl acetate, benzene, diethyl ether, chloroform, methylene chloride, N,N-dimethylformamide or any other solvent which does not adversely influence the reaction.

The reaction temperature is not critical and the reaction may be preferably carried out within a temperature range of cooling to ambient temperature.

Process 7: Elimination of amino-protective group

The compound (IIIc) or its ester or a salt thereof can be prepared by subjecting the compound (IIId) or its ester or a salt thereof to elimination reaction of the amino-protective group.

The reaction may be conducted substantially in the same manner as the aforementioned Process C.

Process 8: Carboxy formation

The compound (IIIf) or its salt can be prepared by transforming the esterified carboxy group of the compound (IIIe) or its salt into free carboxy group, respectively.

The reaction may be conducted substantially in the same manner as aforementioned Process D.

Process 9: Introducing lower alkoxycarbonyl group

The compound (IIIh) or its ester or a salt thereof can be prepared by reacting the compound (IIIg) or its ester or a salt thereof with introducing agent of lower alkoxycarbonyl group.

The suitable example of the introducing agent of lower alkoxycarbonyl group may include 2-(lower)alkoxycarbonylimino-2-cyanoacetamide (e.g., 2-ethoxycarbonyloxyimino-2-cyanoacetamide, 2-isobutoxycarbonyloxyimino-2-cyanoacetamide, etc.), di(lower)alkyl 2-(lower)alkoxycarbonyloxyiminomalonate (e.g., diethyl 2-tert-butoxycarbonyloxyiminomalonate, etc.), lower alkyl 2-(lower)alkoxycarbonyloxyimino-2-cyanoacetate (e.g., ethyl 2-isobutoxycarbonyloxyimino-2-cyanoacetate, etc.), lower alkyl 2-(lower)-alkoxycarbonyloxyiminoacetoacetate (e.g., ethyl 2-tert-butoxycarbonyloxyiminoacetoacetate, etc.), lower alkoxycarbonyloxyimino-2-phenylacetonitrile (e.g., tert-butoxycarbonyloxyimino-2-phenylacetonitrile, etc.) or the like.

The reaction is usually carried out in a solvent such as water, methanol, ethanol, acetone, benzene, diethyl ether, tetrahydrofuran, chloroform, methylene chloride, or any other solvent which does not adversely influence the reaction.

The reaction temperature is not critical, and the reaction may be preferably conducted within a temperature range of cooling to elevated temperature.

This process includes within its scope that the amino for $R^1$ is simultaneously transformed to the alkoxycarbonylamino for $R^1$ in the course of this process or the post-treatment.

Process 10: Elimination of hydroxy-protective group

The compound (IIIj) or its ester or a salt thereof can be prepared by subjecting the compound (IIIi) or its ester or a salt thereof to elimination reaction of the hydroxy protective group in the protected hydroxy group for $R_c^2$.

The reaction may be conducted substantially in the same manner as the aforementioned Process C.

Process 11: Introducing the hydroxy-protective group

The compound (IIIi) or its ester or a salt thereof can be prepared by reacting the compound (IIIj) or its ester or a salt thereof with the introducing agent of hydroxy-protective group.

Suitable introducing agent of the hydroxy-protective group may include an acylating agent.

The reaction can be carried out substantially in the similar manner as aforementioned in Process 6.

This process includes within its scope that the amino for $R^1$ is simultaneously transferred to the protected amino for $R^1$ in the course of this process or the post-treatment.

Following examples are given only for explanation of this invention in more detail.

EXAMPLE A (1) 1,2-Dibromoethane (177 g.) was added dropwise to a stirred mixture of ethyl 2-hydroxyimino-3-oxobutyrate (syn isomer, 100 g.), potassium carbonate (87 g.) and N,N-dimethylformamide (200 ml.) under ice cooling over 10 minutes, and stirred at room temperature for 4 hours. The resultant mixture was filtered and washed with acetone. The filtrate and washings were combined and concentrated in vacuo. After adding water (600 ml.) to the residue, the solution was extracted with methylene chloride three times. The extracts were washed with a saturated aqueous solution of sodium chloride, dried over magnesium sulfate and concentrated in vacuo of give ethyl 2-(2-bromoethoxyimino)-3-oxobutyrate (syn isomer 168 g.), oil.

I.R. $\nu_{max}^{film}$: 1740, 1670, 1500 cm$^{-1}$.

N.M.R. $\delta$(CCl$_4$, ppm): 1.34 (3H, t, J=7 Hz), 2.34 (3H, s), 3.52 (2H, t, J=6 Hz), 4.27 (2H, q, J=7 Hz), 4.48 (2H, t, J=6 Hz).

(2) A mixture of ethyl 2-(2-bromoethoxyimino)-3-oxobutyrate (syn isomer, 168 g.), sulfuryl chloride (87.3 g.) and formic acid (168 ml.) was stirred at 40° C. for 10 minutes and at room temperature for 5.5 hours. After adding water (1 l.) to the resultant solution, the mixture was extracted with methylene chloride. The extract was washed with water, a saturated aqueous solution of sodium bicarbonate and a saturated aqueous solution of sodium chloride in turn, dried over magnesium sulfate, and then concentrated in vacuo to give ethyl 2-(2-bromoethoxyimino)-4-chloro-3-oxobutyrate (syn isomer, 156 g.), oil.

I.R. $\nu_{max}^{film}$: 1735, 1710, 1460, 1435 cm$^{-1}$.

N.M.R. $\delta$(CCl$_4$, ppm): 1.36 (3H, t, J=7 Hz), 3.54 (2H, t, J=6 Hz), 4.1-4.8 (4H, m), 4.48 (2H, s).

(3) A mixture of ethyl 2-(2-bromoethoxyimino)-4-chloro-3-oxobutyrate (syn isomer, 156 g.), thiourea (39.4 g.) sodium acetate trihydrate (70.5 g.), water (300 ml.) and ethanol (500 ml.) was stirred at 40° C. for an hour. The resultant solution was concentrated in vacuo and the resiude was extracted twice with ethyl acetate. The extracts were washed with a saturated aqueous solution of sodium chloride, dried over magnesium sulfate and concentrated in vacuo. After adding diethyl ether (1 l.) to the oily residue, the soluble substance was separated by decantation and the solution was concentrated in vacuo. The residue was crystallized with diisopropyl ether and the precipitates were collected by filtration to give ethyl 2-(2-aminothiazol-4-yl)-2-(2-bromoethoxyimino)acetate (syn isomer, 46.4 g.), mp. 111° to 114° C.

I.R. $\nu_{max}^{Nujol}$: 3440, 3250, 3125, 1725, 1535 cm$^{-1}$.

N.M.R. $\delta$(DMSO-d$_6$, ppm): 1.30 (3H, t, J=7 Hz), 3.65 (2H, t, J=6 Hz), 3.8-4.6 (4H, m), 6.94 (1H, s), 7.15 (2H, broad s).

(4) A mixture of acetic anhydride (15.9 g.) and formic acid (7.15 g.) was stirred at 50° C. for an hour. After cooling, ethyl 2-(2-aminothiazol-4-yl)-2-(2-bromoethoxyimino)acetate (syn isomer, 25 g.) was added to the solution and stirred at room temperature for an hour. The resultant solution was poured into water and extracted with ethyl acetate twice. The extracts were washed with a saturated aqueous solution of sodium chloride, a saturated aqueous solution of sodium bicarbonate (three times) and a saturated aqueous solution of sodium chloride in turn, and dried over magnesium sulfate. After concentrating the solution in vacuo, the oily residue was triturated with a mixture of diisopropyl ether and diethyl ether. The precipitates were collected by filtration to give ethyl 2-(2-formamidothiazol-4-yl)-2-(2-bromoethoxyimino)acetate (syn isomer, 16.75 g.), mp. 95° to 98° C.

I.R. $\nu_{max}^{Nujol}$: 3170, 3110, 3060, 1730, 1695 cm$^{-1}$.

N.M.R. $\delta$(DMSO-d$_6$, ppm): 1.34 (3H, t, J=7 Hz), 3.74 (2H, t, J=6 Hz), 4.1-4.6 (4H, m), 7.70 (1H, s), 8.60 (1H, s), 12.67 (1H, s).

(5) Allyl mercaptan (2.12 g.) was added dropwise to a stirred suspension of ethyl 2-(2-formamidothiazol-4-yl)-2-(2-bromoethoxyimino)acetate (syn isomer, 5 g.) and potassium carbonate (3.95 g.) in N,N dimethylformamide (50 ml.) under ice cooling and stirred at the same temperature for 10 minutes and further at room temperature for 5 hours. After adding water (300 ml.) to the resultant solution, the mixture was extracted with ethyl acetate three times. The extracts were washed twice with a saturated aqueous solution of sodium chloride, dried over magnesium sulfate and concentrated in vacuo. The oily residue was subjected to column chromatography on silica gel and eluted with chloroform. The eluate was concentrated in vacuo to give ethyl 2-(2-allylthioethoxyimino)-2-(2-formamidothiazol-4-yl)acetate (syn isomer, 4.0 g.), mp. 62° to 64° C.

I.R. $\nu_{max}^{Nujol}$: 3170, 3110, 3060, 1730, 1695, 1630 cm$^{-1}$.

N.M.R. $\delta$(DMSO-d$_6$, ppm): 1.32 (3H, t, J=7 Hz), 2.77 (2H, t, J=7 Hz), 3.24 (2H, d, J=7 Hz), 4.0-4.7 (4H, m), 4.9-6.2 (3H, m), 7.64 (1H, s), 8.58 (1H, s), 12.64 (1H, broad s).

(6) A mixture of ethyl 2-(2-allylthioethoxyimino)-2-(2-formamidothiazol-4-yl)acetate (syn isomer, 5.1 g.), methanol (37.2 ml.), 1N-aqueous sodium hydroxide (37.2 ml.) and tetrahydrofuran (35 ml.) was stirred at 35° C. for 5.5 hours. After concentrating the resultant solution in vacuo, the residue was washed with ethyl acetate twice. The aqueous solution was adjusted to pH 1 with 10% hydrochloric acid and extracted with ethyl acetate twice. The extract was washed with a saturated aqueous solution of sodium chloride dried over magnesium sulfate and concentrated in vacuo. The residue was triturated with n-hexane and the precipitates were collected by filtration to give 2-(2-allylthioethoxyimino)-2-(2-formamidothiazol-4-yl)acetic acid (syn isomer, 2.03 g.), mp. 70° to 78° C.

I.R. $\nu_{max}^{KBr}$: 3030 (broad), 1700 (shoulder), 1630, 1545 cm$^{-1}$.

N.M.R. $\delta$(DMSO-d$_6$, ppm): 2.75 (2H, t, J=6 Hz), 3.24 (2H, d, J=7 Hz), 4.29 (2H, t, J=6 Hz), 4.9-6.2 (3H, m), 7.58 (1H, s), 8.56 (1H, s), 12.68 (1H, broad s).

EXAMPLE B (1) Ethyl 2-hydroximino-3-oxobutyrate (syn isomer 40 g.), ethoxyethyl bromide (41.1 g.), potassium carbonate (54.1 g.), N,N-dimethylformamide (65 ml.) and ethylacetate (65 ml.) were treated in a similar manner to that of Example A-(1) to give ethyl 2-(2-ethoxyethoxyimino)-3-oxobutyrate (syn isomer, 56.8 g.).

(2) Ethyl 2-(2-ethoxyethoxyimino)-3-oxobutyrate (syn isomer 56 g.), sulfuryl chloride (32.7 g.) and acetic acid (56 ml.) were treated in a similar manner to that of Example A-(2) to give ethyl 4-chloro-2-(2-ethoxyethoxyimino)-3-oxobutyrate (syn isomer, 57.1 g.).

(3) A mixture of ethyl 4-chloro-2-(2-ethoxyethoxyimino)-3oxobutyrate (syn isomer, 56.5 g.), thiourea (19.4 g.), sodium acetate (20.9 g.), ethanol (140 ml.) and water (140 ml.) was stirred at 40° C. for 5 hours. After removing the ethanol from the resultant solution in vacuo, the aqueous solution was adjusted to pH 6.5 with aqueous sodium bicarbonate and then extracted with ethyl acetate. Conc. hydrochloric acid was added to the stirred ethyl acetate extract under ice-cooling to form the precipitates. The precipitates were collected by filtration washed with chilled water and diethyl ether in turn and dried over phosphorus pentoxide under reduced pressure to give ethyl 2-(2-aminothiazol-4-yl)-2-(2-ethoxyethoxyimino)acetate hydrochloride (syn isomer, 23 g.).

I.R. $\nu_{max}^{Nujol}$: 3400, 3220, 3100, 1725, 1630 cm$^{-1}$.

N.M.R. $\delta$(DMSO-d$_6$, ppm): 1.04 (3H, t, J=7 Hz), 1.24 (3H, t, J=7Hz), 3.4 (2H, q, J=7 Hz), 3.62 (2H, t, J=4 Hz), 4.24 (2H, t, J=4 Hz), 4.32 (2H, q, J=7 Hz), 7.16 (1H, s), 7.88 (2H, broad s).

(4) A suspension of ethyl 2-(2-aminothiazol-4-yl)-2-(2-ethoxyethoxyimino)acetate hydrochloride (syn isomer, 16.9 g.) in a mixture of water (170 ml.) and ethyl acetate (200 ml.) was adjusted to pH 6.5 with sodium bicarbonate and the ethyl acetate layer was separated. The aqueous layer was extracted with ethyl acetate (100 ml.), and the extracts were combined together, washed with a saturated aqueous solution of sodium chloride, dried and then concentrated in vacuo. The oily residue was triturated with n-hexane. The precipitates were collected by filtration and washed with n-hexane to give ethyl 2-(2-aminothiazol-4-yl)-2-(2-ethoxyethoxyimino)acetate (syn isomer, 13 g.).

I.R. $\nu_{max}^{Nujol}$: 3450, 3350, 3150, 3100, 1730, 1720, 1620 cm$^{-1}$.

N.M.R. $\delta$(DMSO-d$_6$, ppm): 1.10 (3H, t, J=7 Hz), 1.28 (3H, t, J=7 Hz), 3.48 (2H, q, J=7 Hz), 3.56 (2H, t, J=4 Hz), 4.20 (2H, t, J=4 Hz), 4.28 (2H, q, J=7 Hz), 6.86 (1H, s), 7.26 (2H, broad s).

(5) Ethyl 2-(2-aminothiazol-4-yl)-2-(2-ethoxyethoxyimino)acetate (syn isomer, 11.5 g.), acetic anhydride (8.2 g.) and formic acid (3.7 g.) were treated in a similar manner to that of Example A-(4) to give ethyl 2-(2-formamidothiazol-4-yl)-2-(2-ethoxyethoxyimino)acetate (syn isomer, 8.6 g.).

I.R. $\nu_{max}^{Nujol}$: 3170, 3140, 3050, 1730, 1700 cm$^{-1}$.

N.M.R. $\delta$(DMSO-d$_6$, ppm): 1.10 (3H, t, J=7 Hz), 1.28 (3H, t, J=7 Hz), 3.42 (2H, q, J=7 Hz), 3.58 (2H, t, J=4 Hz), 4.23 (2H, t, J=4 Hz), 4.30 (2H, q, J=7 Hz). 7.58 (1H, s), 8.52 (1H, s).

(6) A solution of ethyl 2-(2-formamidothiazol-4-yl)-2-(2-ethoxyethoxyimino)acetate (syn isomer, 4.35 g.) in 1N aqueous sodium hydroxide (33 ml.) was stirred below 10° C. for 3 hours. The resultant solution was adjusted to pH 7.0 with conc. hydrochloric acid under ice cooling and washed with ethyl acetate. To the aqueous solution was added ethyl acetate and adjusted to pH 1.5 with hydrochloric acid under ice cooling. The ethyl acetate layer was separated and the aqueous layer was extracted with ethyl acetate. The extracts were combined together, washed with a saturated aqueous solution of sodium chloride, dried and then concentrated in vacuo. The oily residue was dissolved in diethyl ether and n-hexane was added to the solution until the solution became clear. The solution was stirred for an hour, and the precipitates were collected by filtration and washed with n-hexane to give 2-(2-ethoxyethoxyimino)-2-(2-formamidothiazol-4-yl)acetic acid (syn isomer, 3.2 g.).

I.R. $\nu_{max}^{Nujol}$: 3350, 3140, 1740, 1700 cm$^{-1}$.

N.M.R. $\delta$(DMSO-d$_6$, ppm): 1.14 (3H, t, J=7 Hz), 3.50 (2H, q, J=7 Hz), 3.66 (2H, t, J=4 Hz), 4.30 (2H, t, J=4 Hz), 7.58 (1H, s), 8.58 (1H, s).

EXAMPLE C (1) A mixture of 2-hydroxyimino-3-oxobutyrate (syn isomer, 47.1 g.), benzylbromide (61.6 g.), potassium carbonate (62.2 g.), N,N-dimethylformamide (70 ml.) and ethyl acetate (70 ml.) was treated in a similar manner to that of Example A-(1) to give ethyl 2-benzyloxyimino-3-oxobutyrate (syn isomer, 70.0 g.).

(2) A solution of ethyl 2-benzyloxyimino-3-oxobutyrate (syn isomer, 56.0 g.), sulfuryl chloride (40.5 g.) and acetic acid (80 ml.) was treated in a similar manner to that of Example A-(2) to give ethyl 2-benzyloxyimino-4-chloro-3-oxobutyrate (syn isomer, 54.6 g.).

(3) A solution of ethyl 2-benzyloxyimino-4-chloro-3-oxobutyrate (syn isomer, 51.4 g.), thiourea (17.5 g.) and sodium acetate (31.3 g.) in a mixture of water (130 ml.) and ethanol (130 ml.) was stirred at 40° to 45° C. for 2.5 hours. The resultant solution was adjusted to pH 6.5 with aqueous sodium bicarbonate and the precipitates were collected by filtration and washed with diisopropyl ether to give ethyl 2-(2-aminothiazol-4-yl)-2-benzyloxyiminoacetate (syn isomer, 39.78 g.).

I.R. $\nu_{max}^{Nujol}$: 3440, 3240, 3100, 1730, 1680 cm$^{-1}$.

N.M.R. $\delta$(DMSO-d$_6$, ppm): 1.22 (3H, t, J=7 Hz), 4.28 (2H, q, J=7 Hz), 5.14 (2H, s), 6.86 (1H, s), 7.34 (5H, s).

(4) A mixture of ethyl 2-(2-aminothiazol-4-yl)-2-benzyloxyiminoacetate (syn isomer, 35 g.), 1N aqueous sodium hydroxide (172 ml.), methanol (150 ml.) and tetrahydrofuran (150 ml.) was stirred at 35° to 40° C. for 9 hours and at room temperature for 12 hours. After adjusted the resultant solution to pH 6.5 with conc. hydrochloric acid, the solution was concentrated to about ⅔ volume of the initial. The concentrate was adjusted to pH 3.5 with conc. hydrochloric acid under ice cooling, and the precipitates were collected by filtration, washed with water and acetone in turn and then dried over phosphorus pentoxide under reduced pressure to give 2-(2-aminothiazol-4-yl)-2-benzyloxyiminoacetic acid (syn isomer, 11.5 g.).

I.R. $\nu_{max}^{Nujol}$: 3330, 3200, 3100, 1660, 1590 cm$^{-1}$.

N.M.R. $\delta$(DMSO-d$_6$, ppm): 5.20 (2H, s), 6.90 (1H, s), 7.40 (5H, s).

EXAMPLE D (1) A mixture of ethyl 2-hydroxyimino-3-oxobutyrate (syn isomer, 15.7 g.), 2-bromoethyl benzoate (27.5 g.), potassium carbonate (20.7 g.), N,N-dimethylformamide (25 ml.) and ethyl acetate (25 ml.) was treated in a similar manner to that of Example A-(1) to give ethyl 2-(2-benzoyloxyethoxyimino)-3-oxobutyrate (syn isomer, 28 g.).

(2) A solution of 2-(2-benzoyloxyethoxyimino)-3-oxobutyrate (syn isomer, 28 g.), a sulfuryl chloride (13.5 g.) and acetic acid (30 ml.) was treated in a similar manner to that of Example A-(2) to give ethyl 2-(2-benzoyloxyethoxyimino)-4-chloro-3-oxobutyrate (syn isomer, 29 g.).

(3) Ethyl 2-(2-benzoyloxyethoxyimino)-4-chloro-3-oxobutyrate (syn isomer, 20 g.), thiourea (7.76 g.), sodium acetate (8.37 g.), water (75 ml.) and ethanol (75 ml.) were treated in a similar manner to that of Example A-(3) to give ethyl 2-(2-aminothiazol-4-yl)-2-(2-benzoyloxyethoxyimino)acetate (syn isomer, 9 g.).

N.M.R. $\delta$(DMSO-d$_6$, ppm): 1.28 (3H, t, J=7 Hz), 4.34 (2H, q, J=7 Hz), 4.56 (4H, m), 6.44 (2H, broad s), 6.68 (1H, s), 7.68–7.34 (3H, m), 8.06 (2H, d,d, J=8 Hz, 2 Hz).

(4) A solution of ethyl 2-(2-aminothiazol-4-yl)-2-(2-benzoyloxyethoxyimino)acetate (syn isomer, 8.5 g.) in a mixture of 1N aqueous sodium hydroxide (35 ml.), methanol (40 ml.) and tetrahydrofuran (40 ml.) was treated in a similar manner to that of Example C-(4) to give 2-(2-aminothiazol-4-yl)-2-(2-hydroxyethoxyimino)acetic acid (syn isomer, 3.3 g.).

I.R. $\nu_{max}^{Nujol}$: 3350, 3075, 1680, 1620 cm$^{-1}$.

N.M.R. δ(DMSO-d$_6$, ppm): 3.64 (2H, t, J=5 Hz), 4.10 (2H, t, J=5 Hz), 6.84 (1H, s), 7.16 (2H, m).

(5) A solution of formic acid (1.6 g.) and acetic anhydride (3.6 g.) was stirred at 50° C. for an hour. After cooling, 2-(2-aminothiazol-4-yl)-2-(2-hydroxyethoxyimino)acetic acid (syn isomer, 1 g.) was added to the solution and stirred at room temperature for 3 hours. Diisopropyl ether was added to the resultant solution, and the precipitates were filtered out. The filtrate was concentrated in vacuo, and the residue was pulverized with diisopropyl ether. The precipitates were collected by filtration to give 2-(2-formamidothiazol-4-yl)-2-(2-formyloxyethoxyimino)-acetic acid (syn isomer, 0.7 g.).

I.R. $\nu_{max}^{Nujol}$: 3200, 1710, 1690 cm$^{-1}$.

N.M.R. δ(DMSO-d$_6$, ppm): 4.38 (4H, s), 7.58 (1H, s), 8.26 (1H, s), 8.54 (1H, s).

EXAMPLE E

To a solution of 2-(2-formamidothiazol-4-yl)-glyoxylic acid (4.63 g.) and sodium bicarbonate (1.95 g.) in water (230 ml.) was added 2-aminooxyacetamide (2.5 g.) and the mixture was stirred at room temperature for 6 hours while keeping at pH 5. After adjusting the solution to pH 1.5 with 10% hydrochloride acid, the precipitates were collected by filtration, washed with water and dried to give 2-(2-formamidothiazol-4-yl)-2-carbamoylmethoxyiminoacetic acid (syn isomer, 3.6 g.), mp 195° C. (dec.).

I.R. $\nu_{max}^{Nujol}$: 3490, 3180, 3110, 1725, 1685, 1660 cm$^{-1}$.

N.M.R. δ(DMSO-d$_6$, ppm): 4.58 (2H, s), 7.01 (1H, broad s), 7.47 (1H, broad s), 7.64 (1H, s), 8.57 (1H, s), 12.70 (1H, broad s).

EXAMPLE F (1) Phenolphthalein (2 drops) was added to a suspension of 2-aminooxyethylamine.dihydrochloride (1.0 g.) in methanol (10 ml.), and adjusted to pH 6 with 1N sodium methoxide. After removing the precipitates from the solution, 2-(2-formamidothiazol-4-yl)glyoxylic acid (1.04 g.) was added to the filtrate at room temperature and stirred at the same temperature for 5 hours. The precipitates were collected by filtration to give 2-(2-formamidothiazol-4-yl)-2-(2-aminoethoxyimino)acetic acid (syn isomer, 0.80 g.).

I.R. $\nu_{max}^{Nujol}$: 3100, 1680, 1590 cm$^{-1}$.

N.M.R. δ(DMSO-d$_6$, ppm): 3.53 (2H, m), 4.17 (2H, broad s), 7.37 (1H, s), 8.47 (1H, s).

(2) A mixture of 2-(2-formamidothiazol-4-yl)-2-(2-aminoethoxyimino)acetic acid (syn isomer, 0.80 g.) and triethylamine (0.45 g.), in a solution of a saturated aqueous solution of sodium bicarbonate (4 ml.), tetrahydrofuran (35 ml.) and water (25 ml.) was adjusted to pH 8.5 with hydrochloric acid. 2-Phenyl-2-(tert-butoxycarbonyloxyimino)acetonitrile (0.77 g.) was added to the stirred solution and stirred at room temperature for 3 hours. After distilling off tetrahydrofuran from the resultant solution, the aqueous solution was washed with diethyl ether, and adjusted to pH 1.5 with 85% phosphoric acid. The solution was extracted with ethyl acetate (50 ml.), and the extract was washed with a saturated aqueous solution of sodium chloride (10 ml.), dried over magnesium sulfate and concentrated under reduced pressure to give 2-(2-formamidothiazol-4-yl)-2-(2-tert-butoxycarbonylaminoethoxyimino)acetic acid (syn isomer, 0.40 g.).

EXAMPLE G

A mixture of 2-(2-formamidothiazol-4-yl)-glyoxylic acid (1.59 g.), tert-butyl N-aminooxyethylcarbamate (1.40 g.) and methanol (25 ml.) was stirred at room temperature for 6 hours. After removal of methanol from the resultant solution under reduced pressure, the residue was pulverized with diethyl ether. The precipitates were collected by filtration to give 2-(2-formamidothiazol-4-yl)-2-(2-tert-butoxycarbonylaminoethoxyimino)acetic acid (syn isomer, 2.2 g.).

I.R. $\nu_{max}^{Nujol}$: 3140, 1698, 1604 cm$^{-1}$.

N.M.R. δ(DMSO-d$_6$, ppm): 1.37 (9H, s), 3.20 (2H, m), 3.97 (2H, m), 6.73 (1H, broad s), 7.33 (1H, s), 8.50 (1H, s).

EXAMPLE H (1) A mixture of chloromethylthiomethane (7.97 g.), powdered potassium iodide (15.1 g.) and acetone (79 ml.) was stirred at room temperature for an hour, the resulting mixture was filtered and washed with a small amount of acetone. The washings and the filtrate were combined and added to a stirred suspension of ethyl 2-(2-formamidothiazol-4-yl)-2-hydroxyiminoacetate (syn isomer, 17.5 g.) and powdered potassium carbonate (15.5 g.) in acetone (300 ml.). The mixture was stirred at room temperature for 3 hours, filtered and washed with acetone. The washings and the filtrate were combined and concentrated in vacuo. The residue was dissolved in ethyl acetate, washed with a saturated aqueous solution of sodium chloride twice, dried over magnesium sulfate and concentrated in vacuo. The oily residue was subjected to column chromatography on silica gel and eluted with chloroform to give ethyl 2-(2-formamidothiazol-4-yl)-2-methylthiomethoxyiminoacetate (syn isomer, 2.4 g.), mp 130° to 131° C.

I.R. $\nu_{max}^{Nujol}$: 3160, 3125, 3050, 1740, 1695 cm$^{-1}$.

N.M.R. δ(DMSO-d$_6$, ppm): 1.32 (3H, t, J=7 Hz), 2.22 (3H, s), 4.38 (2H, q, J=7 Hz), 5.33 (2H, s), 7.67 (1H, s), 8.56 (1H, s).

(2) A mixture of ethyl 2-(2-formamidothiazol-4-yl)-2-methylthiomethoxyiminoacetate (syn isomer, 2.4 g.), 1N aqueous sodium hydroxide (23.8 ml.) and methanol (19.8 ml.) was stirred at 30° C. for 2.5 hours. The resultant solution was adjusted to pH 7 with 10% hydrochloric acid and methanol was distilled off in vacuo. The aqueous solution was adjusted to pH 1 with 10% hydrochloric acid under ice cooling, and extracted with ethyl acetate three times. The extracts were washed with a saturated aqueous solution of sodium chloride, dried over magnesium sulfate and concentrated in vacuo to give 2-(2-formamidothiazol-4-yl)-2-methylthiomethoxyiminoacetic acid (syn isomer, 1.13 g.), m.p. 157° C. (dec.).

I.R. $\nu_{max}^{Nujol}$: 3210, 3160, 3075, 1700, 1555 cm$^{-1}$.

N.M.R. δ(DMSO-d$_6$, ppm): 2.24 (3H, s), 5.31 (2H, s), 7.61 (1H, s), 8.57 (1H, s), 12.73 (1H, s).

EXAMPLE I (1) Potassium carbonate (4.84 g.) was added to a stirred solution of ethyl 2-(2-tritylaminothiazol-4-yl)-2-hydroxyiminoacetate (syn isomer, 10 g.) in N,N-dimethylformamide (22.0 ml.). Chloroacetonitrile (2.64 g.) was added dropwise to the solution under nitrogen atmosphere and stirred at room temperature for 5 hours. After removing the insoluble substance from the resultant mixture by filtration, water (300 ml.) was added to the filtrate and extracted with ethyl acetate (300 ml.). The extract was washed with a saturated aqueous solution of sodium chloride, dried over magnesium sulfate, treated with activated charcoal and concentrated in vacuo. The residue was pulverized with a mixture of n-hexane, ethyl acetate and acetone (4:4:1) and then the precipitates were collected by filtration and washed with n-hexane to give ethyl 2-(2-tritylaminothiazol-4-yl)-2-cyanomethoxyiminoacetate (syn isomer, 9.58 g.).

I.R. $\nu_{max}^{Nujol}$: 3400, 2200, 1720 cm$^{-1}$.

N.M.R. $\delta$(DMSO-d$_6$, ppm): 1.13 (3H, t, J=7.5 Hz), 4.06 (2H, q, J=7.5 Hz), 5.05 (2H, s), 7.13 (1H, s), 7.13-7.62 (15H, m), 8.92 (1H, s).

(2) A solution of ethyl 2-(2-tritylaminothiazol-4-yl)-2-cyanomethoxyiminoacetate (syn isomer, 4.96 g.) in 90% aqueous formic acid (50 ml.) was stirred at room temperature for 40 minutes. The precipitates were filtered off and washed with diisopropyl ether (20 ml.). The filtrate and the washings were combined together and evaporated in vacuo below 40° C. The residue was washed with benzene (85 ml.) and dried to give ethyl 2-(2-aminothiazol-4-yl)-2-cycanomethoxyiminoacetate (syn isomer, 1.5 g.), m.p. 167° to 168° C.

I.R. $\nu_{max}^{Nujol}$: 3440, 3260, 3120, 1730, 1625 cm$^{-1}$.

N.M.R. $\delta$(DMSO-d$_6$, ppm): 1.32 (3H, t, J=6 Hz), 4.36 (2H, q, J=6 Hz), 5.10 (2H, s), 7.07 (1H, s), 7.37 (2H, s).

EXAMPLE J

A mixture of 2-(2-formamidothiazol-4-yl)glyoxylic acid (5 g.), (3-isoxazolyl)methoxyamine hydrochloride (4.53 g.), sodium bicarbonate (4.2 g.) and water (200 ml.) was stirred at room temperature for 4 hours, while keeping at pH 5.0. After removing the insoluble substance from the resultant mixture by filtration, the filtrate was adjusted to pH 1.5 with 10% hydrochloric acid and stirred at 5° C. for 30 minutes. The precipitates were collected by filtration, washed with water and dried to give 2-(2-formamidothiazol-4-yl)-2-[(3-isoxazolyl)methoxyimino]acetic acid (syn isomer, 5.68 g.), mp. 110° C. (dec.).

I.R. $\nu_{max}^{Nujol}$: 3270, 3130, 1600, 1540 cm$^{-1}$.

N.M.R. $\delta$(DMSO-d$_6$, ppm): 5.38 (2H, s), 6.65 (1H, d, J=2 Hz), 7.67 (1H, s), 8.62 (1H, s), 8.98 (1H, d, J=2 Hz), 12.72 (1H, broad s).

EXAMPLE K (1) Hydrazine hydrate (3.7 g) was added to a solution of N-cyanomethylphthalimide (15.2 g) in ethanol (100 ml) at 50° C. and stirred at 65° to 70° C. for 15 minutes. To the solution were added conc.hydrochloric acid (7.5 ml) and water (10 ml). The insoluble substance was removed by filtration, and the filtrate was adjusted to pH 7 with 10% aqueous sodium hydroxide. 2-(2-Formamidothiazol-4-yl)glyoxylic acid (10 g) was added to the solution and adjusted to pH 4 to 4.5 with a saturated aqueous solution of sodium bicarbonate and stirred for 2 hours. After removing ethanol from the resultant solution in vacuo, ethyl acetate was added to the residue and adjusted to pH 7 with a saturated aqueous solution of sodium bicarbonate. The aqueous layer was separated, adjusted to pH 2 with 10% hydrochloric acid and extracted with ethyl acetate. The extract was washed with a saturated aqueous solution of sodium chloride, dried over magnesium sulfate and concentrated in vacuo. The residue was pulverized with diisopropyl ether to give 2-(2-formamidothiazol-4-yl)-2-cyanomethoxyiminoacetic acid (syn isomer, 8.3 g).

I.R. $\nu_{max}^{Nujol}$: 3260, 1680, 1595, 1540 cm$^{-1}$.

N.M.R. $\delta$(DMSO-d$_6$, ppm): 5.20 (2H, s), 7.73 (1H, s), 8.62 (1H, s).

(2) A solution of 2-(2-formamidothiazol-4-yl)-2-cyanomethoxyiminoacetic acid (syn isomer, 2.54 g) and conc. hydrochloric acid (3 ml) in methanol (30 ml) was stirred at room temperature for an hour. After removing methanol from the resultant mixture in vacuo, water was added to the residue and adjusted to pH 3.3 with an aqueous solution of sodium bicarbonate under ice-cooling. The precipitates were collected by filtration to give 2-(2-aminothiazol-4-yl)-2-cyanomethoxyiminoacetic acid (syn isomer, 2.1 g)

I.R. $\nu_{max}^{Nujol}$: 3250, 1660, 1620 cm$^{-1}$.

N.M.R. $\delta$(DMSO-d$_6$, ppm): 5.10 (2H, s), 7.03 (1H, s).

EXAMPLE L

A mixture of 2-(2-formamidothiazol-4-yl)glyoxylic acid (1.10 g.) and 2-methylthiazol-4-ylmethoxyamine (0.99 g.) in methanol (17 ml.) was stirred at room temperature for 3 hours. The precipitates were collected by filtration and washed with methanol to give 2-(2-formamidothiazol-4-yl)-2-(2-methylthiazol-4-ylmethoxyimino)-acetic acid (synisomer, 1.17 g.).

I.R. $\nu_{max}^{Nujol}$: 1680, 1650, 1618 cm$^{-1}$.

EXAMPLE M (1) Sodium bicarbonate (4.2 g.) was added to a suspension of 2-(2-formamidothiazol-4-yl)glyoxylic acid (10 g.) in water (500 ml.) to prepare a solution. t-Butyl 2-aminoxyacetate hydrochloride (8.1 g.) was added to the solution and stirred at room temperature for 3 hours while adjusting to pH 6 with sodium bicarbonate. The resultant solution was adjusted to pH 1.5 with hydrochloric acid, salted out and extracted with ethyl acetate three times. The extract was dried over magnesium sulfate and concentrated in vacuo. The residue was pulverized with diethyl ether, and the precipitates were collected by filtration and dried to give 2-(2-formamidothiazol-4-yl)-2-t-butoxycarbonylmethoxyiminoacetic acid (syn isomer, 11.3 g.), mp 117° C. (dec.).

I.R. $\nu_{max}^{Nujol}$: 3180, 3140, 1750, 1690, 1630 cm$^{-1}$.

N.M.R. $\delta$(DMSO-d$_6$, ppm): 1.46 (9H, s), 4.66 (2H, s), 7.56 (1H, s), 8.56 (1H, s), 12.67 (1H, broad s).

(2) 2-(2-formamidothiazol-4-yl)-2-t-butoxycarbonylmethoxyiminoacetic acid (syn isomer, 5 g.), N,N-dimethylformamide (1.68 g.), phosphoryl chloride (3.52 g.) and tetrahydrofuran (50 ml.) were treated in a similar manner to that of Example 1(1) to give an activated acid solution. The solution was added to a stined suspension of 4-nitrobenzyl 7-amino-3-cephem-4-carboxylate (5.23 g.), in tetrahydrofuran (26 ml.), acetone (13 ml.) and water (13 ml.) at −5° to 0° C., and stirred at the same temperature for 30 minutes while keeping at pH 7 to 7.5 with 20% aqueous solution of sodium carbonate. After removing the insoluble substance from the resultant mixture, the filtrate was washed with a saturated aqueous solution of sodium chloride and dried over magnesium sulfate. The solution was concentrated in vacuo, and the residue was triturated with diethyl ether. The precipitates were collected by filtration and dried to give 4-nitrobenzyl 7-[2-(2-formamidothiazol-4-yl)-2-t- butoxycarbonylmethoxyiminoacetamido]-3-cephem-4-carboxylate (syn isomer, 10.2 g.)

I.R. $\nu_{max}^{Nujol}$: 3270, 1790, 1735, 1690 cm$^{-1}$.

N.M.R. δ(DMSO-d$_6$, ppm): 1.44 (9H, s), 3.68 (2H, s), 4.62 (2H, s), 5.18 (1H, d, J=5 Hz), 5.42 (2H, s), 5.93 (1H, dd, J=5 Hz), 9 Hz), 6.63 (1H, broad s), 7.40 (1H, s), 7.66 (2H, d, J=9 Hz), 8.26 (2H, d, J=9 Hz), 8.49 (1H, s), 9.56 (1H, d, J=9 Hz), 12.61 (1H, broad s)

(3) Trifluoroacetic acid (40 ml.) was added to a suspension of 4-nitrobenzyl 7-[2-(2-formamidothiazol-4-yl)-2-t-butoxycarbonylmethoxyiminoacetamido]-3-cephem-4-carboxylate (syn isomer, 10 g.) in anisole (10 ml.) at 5° C., and stirred at room temperature for 70 minutes. After evaporating the solvent from the resultant mixture in vacuo, the residue was triturated with diethyl ether. The precipitates were collected by filtration and dried to give 4-nitrobenzyl 7-[2-(2-formamidothiazol-4-yl)-2-carboxymethoxyiminoacetamido]-3-cephem-4-carboxylate (syn isomer, 8.2 g.).

I.R. $\nu_{max}^{Nujol}$: 3260, 3070, 1780, 1730, 1675, 1650 cm$^{-1}$.

N.M.R. δ(DMSO-d$_6$, ppm): 3.33 (2H, d, J=4 Hz), 4.68 (2H, s), 5.22 (1H, d), 5.45 (2H, s), 5.98 (1H, dd, J=5 Hz, 8 Hz), 6.68 (1H, broad s), 7.47 (1H, s), 7.70 (2H, d, J=9 Hz), 8.26 (2H, d), 8.54 (1H, s), 9.64 (1H, d, J=8 Hz), 12.69 (1H, broad s).

EXAMPLE N

The solution of 4-bromo-3-hydroxybenzyloxyamine phosphate (17.4 g.) in water (200 ml.) and ethanol (200 ml.) was stirred at room temperature and adjusted to pH 7.0 with sodium bicarbonate. 2-(2-Formamidothiazol-4-yl)glyoxylic acid (10.0 g.) was added to the solution and the resulting suspension was adjusted to pH 4.0 to 4.5. After stirring the solution at room temperature for 2 hours, ethanol was removed from the resultant solution in vacuo. Ethyl acetate was added to aqueous residue and adjusted to pH 2.5 with 10% hydrochloric acid. The ethyl acetate layer was separated, washed with water and dried over magnesium sulfate. The solution was concentrated in vacuo to give 2-(2-formamidothiazol-4-yl)-2-(4-bromo-3-hydroxybenzyloxyimino)acetic acid (syn isomer, 14.8 g.).

I.R. $\nu_{max}^{Nujol}$: 3350, 3150, 1720, 1680, 1570 cm$^{-1}$.

N.M.R. δ(DMSO-d$_6$, ppm): 5.13 (2H, m), 6.8 (1H, dd, J=8 Hz, 2 Hz), 7.02 (1H, d, J=2 Hz), 7.5 (1H, d, J=8 Hz), 7.58 (1H, s), 8.58 (1H, s), 10.35 (1H, broad s), 12.7 (1H, broad s).

EXAMPLE O (1) A mixture of 1,4-bis(chloromethyl)benzene (25 g.), N-hydroxyphthalimide (23.4 g.) and triethylamine (14.5 g.) in acetonitrile (200 ml.) was heated under reflux for 1.5 hours. The reaction mixture was poured into ice-water (1 l.) and the precipitates were collected by filtration. The precipitates were washed with ethanol and dried to give N-(4-chloromethylbenzyloxy)phthalimide (25.5 g.).

I.R. $\nu_{max}^{Nujol}$: 1780, 1740 cm$^{-1}$.

N.M.R. δ(DMSO-d$_6$, ppm): 4.8 (2H, s), 5.23 (2H, s), 7.22 (4H, s), 7.9 (4H, s).

(2) A mixture of N-(4-chloromethylbenzyloxy)phthalimide (18.5 g.) and potassium phthalimide (15.4 g.) in N,N-dimethylformamide (180 ml.) was stirred at 60° C. for 5 hours. The mixture was poured into ice-water and the precipitates were collected by filtration. The precipitates were washed with water and acetone in turn to give N-(4-phthalimidomethylbenzyloxy)phthalimide (21.0 g.).

I.R. $\nu_{max}^{Nujol}$: 1780, 1760, 1740, 1720, 1610 cm$^{-1}$.

N.M.R. δ(DMSO-d$_6$, ppm): 4.78 (2H, s), 5.13 (2H, s), 7.38 (4H, m), 7.83 (8H, m).

(3) 100% Hydrazine hydrate (4.2 g.) was added to a suspension of N-(4-phthalimidomethylbenzyloxy)phthalimide (16.4 g.) in ethanol (160 ml.) at 60° C. and stirred at the same temperature for an hour. Conc. hydrochloric acid (12 ml.) and water (120 ml.) were added to the resultant mixture under ice-cooling. After filtration of the insoluble substance, the filtrate was concentrated in vacuo. The residue was adjusted to pH 7.0 with 10% sodium hydroxide solution and washed with ethyl acetate. To the aqueous solution containing 4-aminomethylbenzyloxyamine were added 2-(2-formamidothiazol-4-yl)glyoxylic acid (5.3 g.) and ethanol (150 ml.), and the solution was stirred at pH 4.0 to 4.5 for 2.5 hours. The precipitates were collected by filtration and washed with water. The precipitates containing 2-(2-formamidothiazol-4-yl)-2-(4-aminomethylbenzyloxyimino)acetic acid (syn isomer) were added to a mixture of water (100 ml.) and dioxane (100 ml.) and adjusted to pH 8.0 with 10% sodium hydroxide. Triethylamine (3.2 g.) and 2-tert-butoxycarbonyloxyimino-2-phenylacetonitrile (4.7 g.) were added to the mixture and stirred at room temperature for 6 hours. Dioxane was removed in vacuo, and the aqueous residue was washed with diethyl ether. Diethyl ether was added to the aqueous solution and adjusted to pH 3.0 with 10% hydrochloric acid. After removing diethyl ether from the mixture, the residue was washed with a sodium chloride saturated solution, dried over magnesium sulfate and evaporated in vacuo to give 2-(2-formamidothiazol-4-yl)-2-(4-tert-butoxycarbonylaminomethylbenzyloxyimino)acetic acid (syn isomer, 3.8 g.).

I.R. $\nu_{max}^{Nujol}$: 3300, 3150, 1710, 1690, 1620, 1560 cm$^{-1}$. N.M.R. δ(DMSO-d$_6$, ppm): 1.38 (9H, s), 4.15 (2H, d, J=6 Hz), 5.22 (2H, s), 7.6 (1H, s), 7.68 (4H, s), 8.62 (1H, s), 12.8 (1H, broad s).

EXAMPLE P (1) Ethyl 2-hydroxyimino-3-oxobutyrate (syn isomer, 17.0 g.), 2,4-dichlorobenzyl chloride (25 g.), potassium carbonate (22.0 g.), N,N-dimethylformamide (25 ml.) and ethyl acetate (25 ml.) were treated in a similar manner to that of Example A-(1) to give ethyl 2-(2,4-dichlorobenzyloxyimino)-3-oxobutyrate (syn isomer, 33.7 g.)

I.R. $\nu_{max}^{Film}$: 3100, 3000, 2950, 1740, 1700, 1590, 1560 cm$^{-1}$.

(2) Ethyl 2-(2,4-dichlorobenzyloxyimino)-3-oxobutyrate (syn isomer, 33.7 g.), sulfuryl chloride (15.7 g.) and acetic acid (35 ml) treated in a similar manner to that of Example A-(2) to give ethyl 4-chloro-2-(2,4-dichlorobenzyloxyimino)-3-oxobutyrate (syn isomer, 40.5 g.).

I.R. $\nu_{max}^{Film}$: 3100, 3000, 1740, 1710, 1590, 1560 cm$^{-1}$.

(3) Ethyl 4-chloro-2-(2,4-dichlorobenzyloxyimino)-3-oxobutyrate (syn isomer, 37.3 g.), thiourea (8.1 g.), sodium acetate (8.7 g.), ethanol (100 ml.) and water (100 ml.) were treated in a similar manner to that of Example C-(3) to give ethyl 2-(2-aminothiazol-4-yl)-2-(2,4-dichlorobenzyloxyimino)acetate (syn isomer, 12.7 g.).

N.M.R. δ(DMS0-d$_6$, ppm): 1.28(3H, t, J=6 Hz), 4.33(2H, q, J=6 Hz), 5.27(2H, s), 6.95(1H, s), 7.48(2H, s), 7.63(1H, s).

(4) A solution of 1-methylimidazole (0.5 g.) in 1N sodium hydroxide aqueous solution (48 ml.) was added to a solution of ethyl 2-(2-aminothiazol-4-yl)-2-(2,4-dichlorobenzyloxyimino)acetate (syn isomer, 12.0 g.), methanol (120 ml.) and tetrahydrofuran (100 ml.) at 15° to 20° C., and stirred at 35° to 40° C. for 6 hours. After removing methanol and tetrahydrofuran in vacuo from the resultant mixture, the aqueous residue was washed with ethyl acetate. Ethyl acetate was completely removed from the aqueous solution and adjusted to pH 2.0 with hydrochloric acid. The precipitates were collected by filtration to give 2-(2-aminothiazol-4-yl)-2-(2,4-dichlorobenzyloxyimino)acetic acid (syn isomer, 10.0 g.).

N.M.R. δ(DMSO-d$_6$, ppm): 5.28 (2H, s), 6.93 (1H, s), 7.53 (2H, s), 7.67 (1H, s).

(5) Bis(trimethylsilyl)acetamide (13.1 g.) was added dropwise to a stirred solution of 2-(2-aminothiazol-4-yl)-2-(2,4-dichlorobenzyloxyiminoacetic acid (syn isomer, 9.0 g.) in ethyl acetate (90 ml.) at room temperature and stirred at the same temperature for 10 minutes. 2,2,2-trifluoroacetic anhydride (19.5 g.) was added dropwise to a stirred solution at −10° C. over 10 minutes, and stirred at same temperature for 20 minutes, and further at 0° to 5° C. for 2 hours. To the reaction mixture were added water (100 ml.) and ethyl acetate (60 ml.) and then the solution was adjusted to pH 1.5 with sodium bicarbonate saturated aqueous solution. After extracted the solution with ethyl acetate, the extract was washed with sodium chloride saturated aqueous solution and dried over magnesium sulfate. The solution was concentrated in vacuo. The precipitates were washed with diisopropyl ether to give 2-[2-(2,2,2-trifluoroacetamido)thiazol-4-yl]-2-(2,4-dichlorobenzyloxyimino)acetic acid (syn isomer, 10 g.), m.p. 170° to 176° C.

I.R. $\nu_{max}^{Nujol}$: 3200, 1720, 1580 cm$^{-1}$.

N.M.R. δ(DMSO-d$_6$, ppm): 5.28 (2H, s), 7.48 (2H, s), 7.62 (1H, s), 7.7 (1H, s).

EXAMPLE Q (1) Ethyl 2-hydroxyimino-3-oxobutyrate (syn isomer, 40.0 g.), 4-fluorobenzyl chloride (43.6 g.), N,N-dimethylformamide (60.0 ml.), potassium carbonate (52.0 g.) and ethyl acetate. (60.0 ml.) were treated in a similar manner to that of Example A-(1) to give 2-(4-fluorobenzyloxyimino)-3-oxobutyrate (syn isomer, 64.4 g.).

I.R. $\nu_{max}^{Film}$: 3000, 2940, 1730, 1690, 1600 cm$^{-1}$.

N.M.R. δ(DMSO-d$_6$, ppm): 1.21 (3H, t, J=7.0 Hz), 2.34 (3H, s), 4.26 (2H, q, J=7.0 Hz), 5.32 (2H, s), 6.97–7.73 (4H, m).

(2) Ethyl 2-(4-fluorobenzyloxyimino)-3-oxobutyrate (syn isomer, 64.0 g.) and sulfuryl chloride (35.6 g.) and acetic acid (70.0 ml.) were treated in a similar manner to that of Example A-(2) to give ethyl 4-chloro-2-(4-fluorobenzyloxyimino)-3-oxobutyrate (syn isomer, 29.55 g.).

I.R. $\nu_{max}^{Film}$: 1720, 1600 cm$^{-1}$.

N.M.R. δ(DMSO-d$_6$, ppm): 1.20 (3H, t, J=7.0 Hz), 4.28 (2H, q, J=7.0 Hz), 4.87 (2H, s), 5.36 (2H, s), 7.00–7.75 (4H, m).

(3) Ethyl-4-chloro-2-(4-fluorobenzyloxyimino)-3-oxybutyrate (syn isomer, 29.0 g.), thiourea (8.8 g.), sodium acetate (7.9 g.), water (72.5 ml.), tetrahydrofuran (60 ml.) and ethanol (72.5 ml.) were treated in a similar manner to that of Example C-(3) to give ethyl 2-(2-aminothiazol-4-yl)-2-(4-fluorobenzyloxyimino) acetate (syn isomer, 28.0 g.).

I.R. $\nu_{max}^{Nujol}$: 3450, 3150, 3100, 1710, 1620 cm$^{-1}$.

N.M.R. δ(DMSO-d$_6$, ppm): 1.23 (3H, t, J=7.0 Hz), 4.30 (2H, q, J=7.0 Hz), 5.15 (2H, s), 6.90 (1H, s), 6.95–7.60 (4H, m).

(4) Ethyl 2-(2-aminothiazol-4-yl)-2-(4-fluorobenzyloxyimino)-acetate (syn isomer, 25.5 g.), 1-methylimidazole (1.3 g.), 1N sodium hydroxide solution (118.3 ml.), methanol (250 ml.) and tetrahydrofuran (200 ml.) were treated in similar manner to that of Example p-(4) to give 2-(2-aminothiazol-4-yl)-2-(4-fluorobenzyloxyimino)acetic acid (syn isomer, 22.11 g.).

I.R. $\nu_{max}^{Nujol}$: 3650, 3450, 3300, 3150, 1630 cm$^{-1}$.

N.M.R. δ(DMSO-d$_6$, ppm): 5.16 (2H, s), 6.88 (1H, s), 7.04–7.66 (4H, m).

(5) 2-(2-Aminothiazol-4-yl)-2-(4-fluorobenzyloxyimino)acetic acid (syn isomer, 23.4 g.), bis (trimethylsilyl)acetamide (32.2 g.), 2,2,2-trifluoroacetic anhydride (49.9 g.) and dry ethyl acetate (234 ml.) were treated in a similar manner to that of Example P-(5) to give 2-[2-(2,2,2-trifluoroacetamido)thiazol-4-yl]-2-(4-fluorobenzyl-oxyimino)acetic acid (syn isomer, 18.9 g.), m.p. 180°–182° C.

I.R. $\nu_{max}^{Nujol}$: 3200, 3150, 1730 cm$^{-1}$.

N.M.R. δ(DMSO-d$_6$, ppm): 5.25 (2H, s), 7.02–7.60 (4H, m), 7.72 (1H, s).

EXAMPLE R (1) Ethyl 2-hydroxy-3-oxobutyrate (syn isomer, 75.91 g.), 4-methylbenzyl chloride (51.59 g.), potassium carbonate (71 g.), N,N-dimethylformamide (50 ml.) and ethyl acetate (50 ml.) were treated in a similar manner to that of Example A-(1) to give ethyl 2-(4-methylbenzyloxyimino)-3-oxobutyrate (syn isomer, 74.08 g), oil.

I.R. $\nu_{max}^{Film}$: 1740, 1670, 1470, 1260, 1230, 1010 cm$^{-1}$.

N.M.R. δ(CCl$_4$, ppm): 1.27 (3H, t, J=7 Hz), 2.33 (3H, s), 4.23 (2H, q, J=7 Hz), 4.43 (2H, s), 7.10 (4H, s).

(2) A mixture of ethyl 2-(4-methylbenzyloxyimino)-3-oxobutyrate (syn isomer, 74.08 g.), sulfuryl chloride (41.70 g.) and acetic acid (75 ml.) was stirred at at 40° to 42° C. for 4 hours. Nitrogen gas was bubbled into the reaction mixture. After adding the mixture into ice water, the mixture was extracted with methylene chloride. The extract was washed with sodium bicarbonate saturated aqueous solution and sodium chloride saturated aqueous solution in turn and dried over magnesium sulfate. After removing the solvent in vacuo, the residue was allowed to stand in a refrigerator overnight. The precipitates were removed by filtration, and the filtrate was concentrated in vacuo. The residue was subjected to column chromatography on silica gel and eluted with benzene and ethyl acetate. The eluate was concentrated in vacuo to give ethyl 4-chloro-2-(4-methylbenzyloxyimino)-3-oxobutyrate (syn isomer, 19.9 g.). I.R. $\nu_{max}^{Film}$: 3000, 2950, 1740, 1710, 1600, 1440, 1400, 1370, 1340, 1270, 1200, 1000 cm$^{-1}$.

N.M.R. δ(CCl$_4$, ppm): 1.28 (3H, t, J=7 Hz), 2.33 (3H, s), 4.17 (2H, q, J=7 Hz), 4.40 (2H, s), 5.20 (2H, s), 7.13 (4H, s).

(3) Ethyl 4-chloro-2-(4-methylbenzyloxyimino)-3-oxobutyrate (syn isomer, 19.88 g.), thiourea (5.59 g.), sodium acetate (9.99 g.), water (45 ml.) and ethanol (45 ml.) were treated in a similar manner to that of Example P-(3) to give ethyl 2-(2-aminothiazol-4-yl)-2-(4-methyl-benzyloxyimino)-acetate (syn isomer, 8.25 g.).

I.R. $\nu_{max}^{Nujol}$: 3420, 1720, 1610, 1530, 1370, 1290, 1260, 1180, 1020, 1000 cm$^{-1}$.

N.M.R. δ(DMSO-d₆, ppm): 1.27 (3H, t, J=6 Hz), 2.33 (3H, s), 4.33 (2H, q, J=6 Hz), 5.27 (2H, s), 6.93 (1H, s), 7.23 (4H, s).

(4) Ethyl 2-(2-aminothiazol-4-yl)-2-(4-methylbenzyloxyimino)acetate (syn isomer, 4.00 g.), 1N sodium hydroxide solution (19.5 ml.), 1-methylimidazole (214 mg.), methanol (40 ml.) and tetrahydrofuran (25 ml.) were treated in a similar manner that of Example P-(4) to give 2-(2-aminothiazol-4-yl)-2-(4-methylbenzyloxyimino)acetic acid (syn isomer, 3.42 g.).

I.R. $\nu_{max}^{Nujol}$: 1660, 1590–1570, 1360 cm⁻¹.

N.M.R. δ(DMSO-d₆, ppm): 2.30 (3H, s), 5.10 (2H, s), 6.83 (1H, s), 7.20 (4H, s).

(5) 2-(2-Aminothiazol-4-yl)-2-(4-methylbenzyloxyimino)acetic acid (syn isomer, 6.85 g.), bis(trimethylsilyl)acetamide (10.8 g.), 2,2,2-trifluoroacetic anhydride (16.8 g.) and ethyl acetate (70 ml.) were treated in a similar manner to that of Example P-(5) to give 2-[2-(2,2,2-trifluoroacetamido)thiazol-4-yl]-2-(4-methylbenzyloxyimino)acetic acid (syn isomer, 6.58 g.).

I.R. $\nu_{max}^{Nujol}$: 1720, 1580, 1260, 1210, 1200, 1170, 1160, 1000 cm⁻¹.

N.M.R. δ(DMSO-d₆, ppm): 2.33 (3H, s), 5.20 (2H, s), 7.27 (4H, s), 7.70 (1H, s).

EXAMPLE S (1) Ethyl 2-hydroxy-3-oxobutyrate (syn isomer, 74.12 g.), 4-chlorobenzyl chloride (50.0 g.), potassium carbonate (64.4 g.), N,N-dimethylformamide (50 ml.), and ethyl acetate (50 ml.) were treated in a similar manner to that of Example A-(1) to give ethyl 2-(4-chlorobenzyloxyimino)-3-oxobutyrate (syn isomer, 75.93 g.).

N.M.R. δ(CCl₄, ppm): 1.30 (3H, t, J=7 Hz), 2.30 (3H, s), 4.27 (2H, q, J=7 Hz), 4.47 (2H, s), 7.27 (4H, s).

(2) Sulfuryl chloride (39.26 g.) was added to a solution of ethyl 2-(4-chlorobenzyloxyimino)-3-oxobutyrate (syn isomer, 75.03 g.), in acetic acid (75 ml.), and then stirred at 37° to 40° C. for 8 hours. After air was bubbled into the reaction mixture, the mixture was added to ice water. The mixture was extracted with methylene chloride, and the extract was washed with sodium bicarbonate saturated aqueous solution and sodium chloride saturated aqueous solution in turn. The solution was dried over magnesium sulfate and concentrated in vacuo to give ethyl 4-chloro-2-(4-chlorobenzyloxyimino)-3-oxobutyrate (syn isomer, 77.23 g.).

I.R. $\nu_{max}^{Film}$: 1740, 1600, 1490, 1260, 1100, 1010 cm⁻¹.

N.M.R. δ(CCl₄, ppm): 1.37 (3H, t, J=7 Hz), 4.23 (2H, q, J=7 Hz), 4.30 (2H, s), 5.27 (2H, s), 7.30 (4H, s)

(3) Ethyl 4-chloro-2-(4-chlorobenzyloxyimino)-3-oxobutyrate (syn isomer, 37.2 g.), thiourea (9.82 g.), sodium acetate 3 hydrate (17.55 g.), water (80 ml.) and ethanol (80 ml.) were treated in similar manner to that of Example P-(3) to give ethyl 2-(2-aminothiazol-4-yl)-2-(4-chlorobenzyloxyimino)acetate (syn isomer, 12.86 g.).

I.R. $\nu_{max}^{Nujol}$: 3440, 1720, 1610, 1530, 1290, 1270, 1180, 1020, 1000 cm⁻¹.

N.M.R. δ(DMSO-d₆, ppm): 1.24 (3H, t, J=6 Hz), 4.32 (2H, q, J=6 Hz), 5.18 (2H, s), 6.98 (1H, s), 7.40 (4H, s)

(4) Ethyl 2-(2-aminothiazol-4-yl)-2-(4-chlorobenzyloxyimino)acetate (syn isomer, 21.15 g.), 1N sodium hydroxide aqueous solution (94 ml.), 1-methylimidazole (1.02 g.), methanol (220 ml.) and tetrahydrofuran (150 ml.) were treated in a similar manner to that of Example P-(4) to give 2-(2-aminothiazol-4-yl)-2-(4-chlorobenzyloxyimino)acetic acid (syn isomer, 10.13 g.).

I.R. $\nu_{max}^{Nujol}$: 3640, 1650 (sh), 1620, 1030, 1010, 1000, 800 cm⁻¹.

N.M.R. δ(DMSO-d₆, ppm): 5.20 (2H, s), 6.90 (1H, s), 7.43 (4H, s).

(5) 2-(2-Aminothiazol-4-yl)-2-(4-chlorobenzyloxyimino)acetic acid (syn isomer, 17.3 g.), bis (trimethylsilyl)acetamide (32.3 g.), 2,2,2-trifluoroacetic anhydride (53.6 g.) and ethyl acetate (170 ml.) were treated in a similar manner to that of Example P-(5) to give 2-[2-(2,2,2-trifluoroacetamido)thiazol-4-yl]-2-(4-chlorobenzyloxyimino)acetic acid (syn isomer, 14.94 g.).

I.R. $\nu_{max}^{Nujol}$: 1720, 1600–1570, 1490, 1350, 1300, 1260, 1200 cm⁻¹.

N.M.R. δ(DMSO-d₆, ppm): 5.27 (2H, s), 7.47 (4H, s), 7.73 (1H, s).

EXAMPLE 1

(1) Phosphoryl chloride (0.754 g.) was added dropwise to a solution of N,N-dimethylformamide (0.36 g.) in ethyl acetate (2 ml.) at −10° to −5° C. and stirred at the same temperature for 30 minutes. Ethyl acetate (13 ml.) and 2-(2-formamidothiazol-4-yl)-2-methylthiomethoxyiminoacetic acid (syn isomer, 1.13 g.) were added to the mixture at −10° to −5° C. and stirred at the same temperature for 30 minutes to give an activated acid solution. The solution was added to a solution of 7-amino-3-cephem-4-carboxylic acid (0.82 g.) and bis(trimethylsilyl)acetamido (4.17 g.) in ethyl acetate (8.2 ml.) at −20° C. and the resulting reaction mixture was stirred at −10° to −5° C. for 30 minutes. After adding water to the resultant solution, the mixture was extracted twice with ethyl acetate. The extracts were washed with a saturated aqueous solution of sodium chloride, dried over magnesium sulfate and concentrated in vacuo. The residue was pulverized with diisopropyl ether, and the precipitates were collected by filtration and dried to give 7-[2-(2-formamidothiazol-4-yl)-2-methylthiomethoxyiminoacetamido]-3-cephem-4-carboxylic acid (syn isomer, 0.26 g.).

I.R. $\nu_{max}^{Nujol}$: 3200 (broad), 1780, 1690, 1540 cm⁻¹.

N.M.R. δ(DMSO-d₆, ppm): 2.21 (3H, s), 3.60 (2H, s), 5.14 (1H, d, J=5 Hz), 5.29 (2H, s), 5.88 (1H, d,d, J=5 Hz, 8 Hz), 6.48 (1H, t, J=3 Hz), 7.59 (1H, s), 8.53 (1H, s), 9.76 (1H, d, J=8 Hz), 12.62 (1H, broad s).

(2) A mixture of 7-[2-(2-formamidothiazol-4-yl)-2-methylthiomethoxyiminoacetamido]-3-cephem-4-carboxylic acid (syn isomer, 0.22 g.), conc. hydrochloric acid (0.25 g.) and methanol (3.3 ml.) was stirred at room temperature for 2.3 hours. After concentrating the resultant solution in vacuo, the residue was poured into water, adjusted to pH 7 with 10% aqueous sodium hydroxide and washed with ethyl acetate. The aqueous solution was adjusted to pH 3 with 10% hydrochloric acid under ice cooling and stirred at the same temperature for 30 minutes. The precipitates were collected by filtration, washed with water and dried to give 7-[2-(2-aminothiazol-4-yl)-2-methylthiomethoxyiminoacetamido]-3-cephem-4-carboxylic acid (syn isomer, 0.1 g.).

I.R. $\nu_{max}^{Nujol}$: 3400, 3250, 1770, 1655, 1620 cm⁻¹.

N.M.R. δ(DMSO-d₆, ppm): 2.20 (3H, s), 3.59 (2H, d, J=4 Hz), 5.12 (1H, d, J=5 Hz), 5.19 (2H, s), 5.83 (1H, d,d, J=5 Hz, 8 Hz), 6.48 (1H, t, J=5 Hz), 6.78 (1H, s), 7.28 (2H, s), 9.63 (1H, d, J=8 Hz).

EXAMPLE 2

(1) A solution of 7-amino-3-cephem-4-carboxylic acid (1.2 g.) and trimethylsilylacetamide (6.3 g.) in ethyl acetate (40 ml.) and a solution of 2-(2-formamidothiazol-4-yl)-2-(2-formyloxyethoxyimino)-acetic acid (syn isomer, 1.72 g.), N,N-dimethylformamide (0.48 g.) and phosphoryl chloride (1.61 g.) in ethyl acetate (22 ml.) were treated in a similar manner to that of Example 1-(1) to give 7-[2-(2-formamidothiazol-4-yl)-4-(2-formyloxyethoxyimino)acetamido]-3-cephem-4-carboxylic acid (syn isomer, 2.2 g.).

N.M.R. δ(DMSO-$d_6$, ppm): 3.60 (2H, broad s), 4.36 (4H, s), 5.12 (1H, d, J=4 Hz), 5.86 (1H, d,d, J=4 Hz, 8 Hz), 6.48 (1H, m), 7.43 (1H, s), 8.22 (1H, s), 8.5 (1H, s), 9.66 (1H, d. J=8 Hz)

(2) A mixture of 7-[2-(2-formamidothiazol-4-yl)-2-(2-formyloxyethoxyimino)acetamido]-3-cephem-4-carboxylic acid (syn isomer, 2.1 g.), conc. hydrochloric acid (1.8 ml.), methanol (15 ml.) and tetrahydrofuran (15 ml.) was stirred at room temperature for 5 hours. After removing the solvent in vacuo, water was added to the residue and adjusted to pH 4.0 with an aqueous solution of sodium bicarbonate. The solution was subjected to column chromatography on nonionic adsorption resin "Diaion HP-20" (trademark, manufactured by Mitsubishi Chemical Industries Ltd.) and eluted with 20% isopropyl alcohol. The eluate was concentrated in vacuo and the residue was lyophilized to give 7-[2-(2-aminothiazol-4-yl)-2-(2-hydroxyethoxyimino)acetamido]-3-cephem-4-carboxylic acid (syn isomer, 0.56 g.).

I.R. $\nu_{max}^{Nujol}$: 3340, 3230, 1775, 1660 cm$^{-1}$.

N.M.R. δ(DMSO-$d_6$): 3.63 (4H, m), 4.10 (2H, m), 5.17 (1H, d, J=4 Hz), 5.83 (1H, d,d, J=4 Hz, 8 Hz), 6.48 (1H, m), 6.75 (1H, s), 7.22 (2H, broad s), 9.48 (1H, d, J=8 Hz).

EXAMPLE 3

(1) A solution of 7-amino-3-cephem-4-carboxylic acid (1.3 g.) and trimethylsilylacetamide (7.0 g.) in ethyl acetate (30 ml.) and a solution of 2-(2-formamidothiazol-4-yl)-2-(2-ethoxyethoxyimino)acetic acid (syn isomer, 1.72 g.), N,N-dimethylformamide (0.48 g.) and phosphoryl chloride (1.01 g.) in ethyl acetate (25 ml.) were treated in a similar manner to that of Example 1-(1) to give 7-[2-(2-formamidothiazol-4-yl)-2-(2-ethoxyethoxyimino)acetamido]-3-cephem-4-carboxylic acid (syn isomer, 2.35 g.).

I.R. $\nu_{max}^{Nujol}$: 3100, 1785, 1720 (shoulder), 1680 cm$^{-1}$.

N.M.R. δ(DMSO-$d_6$, ppm): 1.13 (3H, t, J=7 Hz), 3.83-3.23 (6H, m), 4.28 (2H, t, J=4 Hz), 5.17 (1H, d, J=5 Hz), 5.90 (1H, d,d, J=5 Hz, 8 Hz), 6.53 (1H, m), 7.45 (1H, s), 8.57 (1H, s), 9.70 (1H, d, J=8 Hz).

(2) A mixture of 7-[2-(2-formamidothiazol-4-yl)-2-(2-ethoxyethoxyimino)acetamido]-3-cephem-4-carboxylic acid (syn isomer, 2.2 g.), conc hydrochloric acid (2 ml.) and methanol (30 ml.) was stirred at room temperature for 1.6 hours. After concentrating the resultant solution in vacuo, water was added to the residue, adjusted to pH 6.5 with sodium bicarbonate and washed with ethyl acetate. The aqueous solution was treated with activated charcoal and adjusted to pH 3.0 with conc. hydrochloric acid. The precipitates were collected by filtration, washed with water and dried over phosphorus pentoxide under reduced pressure to give 7-[2-(2-aminothiazol-4-yl)-2-(2-ethoxyethoxyimino)acetamido]-3-cephem-4-carboxylic acid (syn isomer, 0.87 g.).

I.R. $\nu_{max}^{Nujol}$: 3310, 1760, 1650 cm$^{-1}$.

N.M.R. δ(DMSO-$d_6$: ppm): 1.12 (3H, t, J=7 Hz), 3.87-3.28 (6H, m), 4.22 (2H, t, J=4 Hz), 5.13 (1H, d, J=5 Hz), 5.83 (1H, d,d, J=8 Hz, 5 Hz), 6.52 (1H, m), 6.73 (1H, s), 7.27 (2H, broad s), 9.58 (1H, d, J=8 Hz)

EXAMPLE 4

(1) N,N-Dimethylformamide (0.19 g.), phosphorylchloride (0.40 g.), 2-(2-formamidothiazol-4-yl)-2-(2-tert-butoxycarbonylaminoethoxyimino)acetic acid (syn isomer, 0.72 g.) and ethyl acetate (8.5 ml.) were treated in a similar manner to that of Example 1-(1) to give an activated acid solution. The solution was added to a solution of 7-amino-3-cephem-4-carboxylic acid (0.40 g.), trimethylsilylacetamide (1.35 g.), and bis(trimethylsilyl)acetamide (1.2 ml.) in ethyl acetate (4 ml.) at −10° C., and stirred at the same temperature for 1.5 hours. Water (10 ml.) and ethyl acetate (7 ml.) were added to the resultant solution, and the ethyl acetate layer was separated, extracted with a saturated aqueous solution of sodium bicarbonate (10 ml.). The extract was adjusted to pH 5.0 with 85% phosphoric acid and extracted with ethyl acetate (50 ml.). The extract was dried over magnesium sulfate and concentrated in vacuo to give 7-[2-(2-formamidothiazol-4-yl)-2-(2-tert-butoxycarbonylaminoethoxyimino)acetamido]-3-cephem-4-carboxylic acid (syn isomer, 0.65 g.).

I.R. $\nu_{max}^{Nujol}$: 3220, 3050, 1780, 1680 cm$^{-1}$.

N.M.R. δ(DMSO-$d_6$, ppm): 1.33 (9H, s), 3.22 (2H, m), 3.57 (2H, broad s), 4.07 (2H, m), 5.10 (1H, d, J=5 Hz), 5.83 (1H, d,d, J=5 Hz, 8 Hz), 6.45 (1H, t, J=5 Hz), 7.37 (1H, s), 8.50 (1H, s), 9.50 (1H, d, J=8 Hz).

(2) A mixture of 7-[2-(2-formamidothiazol-4-yl)-2-(2-tert-butoxycarbonylaminoethoxyimino)acetamido]-3-cephem-4-carboxylic acid (syn isomer, 0.70 g.), conc. hydrochloric acid (0.48 g.) and methanol (7 ml.) was stirred at room temperature for 4 hours. After concentrating the resultant solution in vacuo, the residue was dissolved in methanol (10 ml.) and crystallized by adding diisopropyl ether (20 ml.). The precipitates were collected by filtration, washed with a mixture of methanol and diisopropyl ether (1:1) and dried to give 7-[2-(2-aminothiazol-4-yl)-2-(2-aminoethoxyimino)acetamido]-3-cephem-4-carboxylic acid dihydrochloride (syn isomer, 0.58 g.).

I.R. $\nu_{max}^{Nujol}$: 3380, 3180, 1770, 1630 cm$^{-1}$.

N.M.R. δ(DMSO-$d_6$, ppm): 3.23 (2H, m), 3.65 (2H, broad s), 4.40 (2H, m), 5.12 (1H, d, J=5 Hz), 5.82 (1H, d,d, J=5 Hz, 8 Hz), 6.52 (1H, t, J=5 Hz), 7.04 (1H, s), 8.37 (2H, broad s), 9.86 (1H, d, J=8 Hz).

EXAMPLE 5

(1) 2-(2-Formamidothiazol-4-yl)-2-allylthioethoxyiminoacetic acid (syn isomer, 1.95 g.), N,N-dimethylformamide (0.543 g.), phosphoryl chloride (1.14 g.) and tetrahydrofuran (19 ml.) were treated in a similar manner to that of Example 1-(1) to give an activated acid solution. A suspension of 7-amino-3-cephem-4-carboxylic acid (1.24 g.) in a mixture of acetone (12.4 ml.) and water (6.2 ml.) was adjusted to pH 7 with 20% aqueous sodium carbonate. To the solution was added dropwise the activated acid solution at −5° to 0° C. while keeping at pH 7.0 to 7.5 and stirred at the same temperature for 30 minutes. After distilling off the organic solvent in vacuo, the aqueous solution was adjusted to pH 2 with 10% hydrochloric acid and extracted with ethyl acetate twice. The extract was washed with a saturated aqueous solution of sodium chloride, dried over magnesium sulfate and concentrated in vacuo. The residue was pulverized with diethyl ether and the precipitates were collected by filtration to give 7-[2-(2-formamidothiazol-4-yl)-2-(2-allylthioethoxyimino)acetamido]-3-cephem-4-carboxylic acid (syn isomer, 2.1 g.).

I.R. $\nu_{max}^{Nujol}$: 3250, 3050, 1780, 1695, 1655, 1630 cm$^{-1}$.

N.M.R. $\delta$(DMSO-d$_6$, ppm): 2.77 (2H, t, J=7 Hz), 3.23 (2H, d, J=7 Hz), 3.61 (2H, d, J=4 Hz), 4.27 (2H, t, J=7 Hz), 4.9–5.4 (3H, m), 5.4–6.2 (2H, m), 6.50 (1H, t, J=5 Hz), 7.44 (1H, s), 8.53 (1H, s), 9.65 (1H, d, J=9 Hz), 12.68 (1H, broad s).

(2) 7-[2-(2-Formamidothiazol-4-yl)-2-(2-allylthioethoxyimino)acetamido]-3-cephem-4-carboxylic acid (syn isomer, 1.5 g.), conc. hydrochloric acid (1.19 g.), tetrahydrofuran (7.5 g.) and methanol (22.5 ml.) were treated in a similar manner to that of Example 1-(2) to give 7-[2-(2-aminothiazol-4-yl)-2-(2-allylthioethoxyimino)acetamido]-3-cephem-4-carboxylic acid (syn isomer, 1.2 g.), powder.

I.R. $\nu_{max}^{Nujol}$: 3160, 1775, 1655, 1530 cm$^{-1}$.

N.M.R. $\delta$(DMSO-d$_6$, ppm): 2.71 (2H, t, J=7 Hz), 3.17 (2H, d, J=7 Hz), 3.58 (2H, s), 4.18 (2H, t, J=7 Hz), 4.8–5.3 (3H, m), 5.4–6.0 (2H, m), 6.47 (1H, t, J=4 Hz), 6.74 (1H, s), 7.22 (2H, s), 9.54 (1H, d, J=9 Hz)

EXAMPLE 6

(1) 2-(2-Formamidothiazol-4-yl)-2-carbamoylmethoxyiminoacetic acid (syn isomer, 1.2 g.), N,N-dimethylformamide (0.768 g.), phosphoryl chloride (1.61 g.) and tetrahydrofuran (2.4 ml.) were treated in a similar manner to that of Example 1-(1) to give an activated acid solution. A suspension of 7-amino-3-cephem-4-carboxylic acid (0.89 g.) in a mixture of tetrahydrofuran (8.9 ml.), acetone (4.5 ml.) and water (4.5 ml.) was adjusted to pH 7 to 8 with 20% aqueous sodium carbonate. The activated acid solution was added to the solution at −5° to 0° C. while keeping at pH 7 to 8 and stirred at the same temperature for 30 minutes. The resultant solution was concentrated in vacuo, and water and ethyl acetate were added to the residue. The solution was adjusted to pH 2.5 and extracted with ethyl acetate. The extract was washed with a saturated aqueous solution of sodium chloride, dried over magnesium sulfate and concentrated in vacuo. The residue was pulverized with diethyl ether, collected by filtration and dried to give 7-[2-(2-formamidothiazol-4-yl)-2-cyanomethoxyiminoacetamido]-3-cephem-4-carboxylic acid (syn isomer, 0.95 g).

I.R. $\nu_{max}^{Nujol}$: 3280, 3180, 3120, 3070, 1790, 1690, 1655 cm $^{-1}$.

N.M.R. $\delta$(DMSO-d$_6$, ppm): 3.62 (2H, s), 5.08 (2H, s), 5.15 (1H, d, J=5Hz), 5.87 (1H, d, d, J=5 Hz, 9 Hz), 6.52 (1H, broad s), 7.56 (1H, s), 8.56 (1H, s), 9.91 (1H, d, J=9 Hz), 12.67 (1H, s).

(2) 7-[2-(2-Formamidothiazol-4-yl)-2-cyanomethoxyiminoacetamido]-3-cephem-4-carboxylic acid (syn isomer, 0.9 g.), conc. hydrochloric acid (0.82 g.), methanol (13.3 ml.) and tetrahydrofuran (25 ml.) were treated in a similar manner to that of Example 1-(2) to give 7-[2-(2-aminothiazol-4-yl)-2-cyanomethoxyiminoacetamido]-3-cephem-4-carboxylic acid (syn isomer, 0.75 g.).

I.R. $\nu_{max}^{Nujol}$: 3480, 3330, 3200, 3090, 1790, 1700, 1660, 1625 cm$^{-1}$.

N.M.R. $\delta$(DMSO-d$_6$, ppm): 3.60 (2H, broad s), 5.01 (2H, s), 5.12 (1H, d, J=5 Hz), 5.82 (1H, d, d, J=5 Hz, 9 Hz), 6.48 (1H, broad s), 6.88 (1H, s), 7.32 (2H, s), 9.79 (1H, d, J=9 Hz).

EXAMPLE 7

(1) A solution of 4-nitrobenzyl 7-amino-3-cephem-4-carboxylate (3.35 g.) and trimethylsilylacetamide (9.2 g.) in ethyl acetate (50 ml.) and a solution of 2-(2-aminothiazol-4-yl)-2-benzyloxyiminoacetic acid (syn isomer, 2.77 g.), trimethylsilylacetamide (0.9 g.), N,N-dimethylformamide (0.9 g.) and phosphoryl chloride (3.84 g.) in tetrahydrofuran (30 ml.) were treated in a similar manner to that of Example 4 to give 4-nitrobenzyl 7-[2-(2-aminothiazol-4-yl)-2-benzyloxyiminoacetamido]-3-cephem-4-carboxylate (syn isomer, 2.85 g.).

I.R. $\nu_{max}^{Nujol}$: 3350, 1790, 1740, 1680 cm$^{-1}$.

N.M.R. $\delta$(DMSO-d$_6$, ppm): 3.28 (2H, m), 5.15 (2H, s), 5.17 (1H, d, J=5 Hz), 5.40 (2H, s), 5.93 (1H, d, d, J=5 Hz, 9 Hz), 6.65 (1H, m), 6.73 (1H, s), 7.23 (5H, s), 7.70 (2H, d, J=8 Hz), 8.25 (2H, d, J=8 Hz), 9.57 (1H, d, J=9 Hz).

(2) A mixture of 4-nitrobenzyl 7-[2-(2-aminothiazol-4-yl)-2-benzyloxyiminoacetamido]-3-cephem-4-carboxylate (syn isomer, 2.7 g.), 10% palladium carbon (1 g.), acetic acid (1 ml.), water (4 ml.), methanol (20 ml.) and tetrahydrofuran (30 ml.) was subjected to catalytic reduction at room temperature under ordinary pressure for 6 hours. After removing the insoluble substance from the resultant mixture by filtration, the filtrate was concentrated in vacuo. Water was added to the residue and adjusted to pH 7 to 8 with sodium bicarbonate, and the insoluble substance was filtered out. The filtrate was washed with ethyl acetate and adjusted to pH 3.0 with conc. hydrochloric acid under ice cooling. The precipitates were collected by filtration, washed with water and dried over phosphorus pentoxide to give 7-[2-(2-aminothiazol-4-yl)-2-benzyloxyiminoacetamido]-3-cephem-4-carboxylic acid (syn isomer, 1.1 g.).

I.R. $\nu_{max}^{Nujol}$: 3300, 1780, 1650 cm$^{-1}$.

N.M.R. $\delta$(DMSO-d$_6$, ppm) 3.58 (2H, broad s), 5.08 (1H, d, J=5 Hz), 5.16 (2H, s), 5.80 (1H, d, d, J=9 Hz, 5 Hz), 6.46 (1H, m), 6.74 (1H, s), 7.36 (5H, s), 9.6 (1H, d, J=9 Hz).

EXAMPLE 8

(1) Phosphoryl chloride (1.02 g.), 2-(2-formamidothiazol-4-yl)-2-(3-isoxazolylmethoxyimino)acetic acid (syn isomer, 1.0 g), N,N-dimethylformamide (0.448 g.) and tetrahydrofuran (10 ml.) were treated in a similar manner to that of Example 5-(1) to give an activated acid solution. On the other hand, a mixture of 7-amino-3-cephem-4-carboxylic acid (0.91 g.), tetrahydrofuran (10 ml.) acetone (5 ml.) and water (5 ml.) was adjusted to pH 7.5 with 20% aqueous sodium carbonate at 0° to −5° C. The activated acid solution was added dropwise to the above solution at 0° to −5° C. while keeping at pH 7.5 to 8.0. The mixture was treated in a similar manner to that of Example 5-(1) to give 7-[2-(2-formamidothiazol-4-yl)-2-(3-isoxazolylmethoxyimino)acetamido]-3-cephem-4-carboxylic acid (syn isomer, 1.25 g.).

I.R. $\nu_{max}^{Nujol}$: 3230 (broad), 3060, 1780, 1690, 1660 cm$^-$.

N.M.R. $\delta$(DMSO-d$_6$, ppm): 3.62 (2H, broad s), 5.16 (1H, d, J=5 Hz), 5.32 (2H, s), 5.93 (1H, d, d, J=5 Hz, 8 Hz), 6.53 (1H, broad s), 6.70 (1H, d, J=2 Hz), 7.50 (1H, s), 8.56 (1H, s), 8.91 (1H, d, J=2 Hz),9.82 (1H, d, J=8 Hz)

(2) A solution of 7-[2-(2-formamidothiazol-4-yl)-2-(3-isoxazolylmethoxyimino)acetamido]-3-cephem-4-carboxylic acid (syn isomer, 1.20 g.) and conc. hydrochloric acid (1.09 g.) in methanol (18 ml.) and tetrahydrofuran (9 ml.) in methanol (18 ml.) and tetrahydrofuran (9 ml.) was stirred at room temperature for 2 hours. The solution was treated in a similar manner to that of Example 5-(2) to give 7-[2-(2-aminothiazol-4-yl)-2-(3-isoxazolylmethoxyimino)acetamido]-3-cephem-4-carboxylic acid (syn isomer, 0.83 g.).

I.R. $\nu_{max}^{Nujol}$: 3460, 3320, 3150, 3080, 1780, 1660, 1630 cm$^{-1}$.

N.M.R. δ(DMSO-d$_6$, ppm): 3.62 (2H, broad s), 5.12 (1H, d, J=5 Hz), 5.25 (2H, s), 5.86 (1H, d, d, J=5 Hz), 6.49 (1H, t, J=4 Hz), 6.64 (1H, d, J=2 Hz), 6.81 (1H, s), 7.27 (2H, broad s), 8.88 (1H, d, J=2 Hz), 9.67 (1H, d, J=8 Hz).

EXAMPLE 9

(1) Tetrahydrofuran (24 ml.) and 4-nitrobenzyl 7-[2-(2-formamidothiazol-4-yl)-2-carboxymethoxyiminoacetamido]-3-cephem-4-carboxylate (syn isomer, 3.07 g.) were added to Vilsmeier reagent prepared from N,N-dimethylformamide (0.0756 g.) and phosphoryl chloride (1.59 g.) in tetrahydrofuran (6 ml.) at −10° t −5° C. and then stirred at the same temperature for 30 minutes. The solution was added dropwise to a mixture of tetrahydrofuran (50 ml.) and water (25 ml.) at −5° to 0° C. while keeping at pH 9 to 9.5 with aqueous ammonia, and stirred for 20 minutes at pH 7.5 After adjusting the resultant solution to pH 2.0 with 10% hydrochloric acid, tetrahydrofuran was removed in vacuo. Water was added to the residue and extracted with ethyl acetate. The extract was washed with a saturated aqueous solution of sodium chloride twice, an aqueous solution of sodium bicarbonate five times and a saturated aqueous solution of sodium chloride twice in turn, dried over magnesium sulfate and then concentrated in vacuo. The residue was pulverized with diethyl ether, collected by filtration and dried to give 4-nitrobenzyl 7-[2-(2-formamidothiazol-4-yl)-2-carbamoylmethoxyiminoacetamido]-3-cephem-4-carboxylate (syn isomer, 1.8 g.).

I.R. $\nu_{max}^{Nujol}$: 3250, 1775, 1720, 1670 cm$^{-1}$.

N.M.R. δ(DMSO-d$_6$, ppm): 3.62 (2H, s), 4.44 (2H, s), 5.13 (1H, d, J=5 Hz), 5.36 (2H, s), 5.89 (1H, d, d, J=5 Hz, 9 Hz), 6.58 (1H, broad s), 7.06 (2H, broad s), 7.40 (1H, s), 7.58 (2H, d, J=9 Hz), 8.12 (2H, d, J=9 Hz), 8.40 (1H, s), 9.78 (1H, d, J=9 Hz).

(2) A suspension of 4-nitrobenzyl 7-[2-(2-formamidothiazol-4-yl)-2-carbamoylmethoxyiminoacetamido]-3-cephem-4-carboxylate (syn isomer, 2.4 g.), 10% palladium-carbon (0.96 g.), acetic acid (0.17 ml.), methanol (9.6 ml.), water (1.7 ml) and tetrahydrofuran (24 ml.) was subjected to catalytic reduction under ordinary pressure for 3 hours. After filtration, the filtrate was concentrated in vacuo. Water and ethyl acetate were added to the residue and adjusted to pH 7.5 with sodium bicarbonate. After filtration, the filtrate was washed with ethyl acetate and diethyl ether in turn, adjusted to pH 1.0 with 10% hydrochloric acid and stirred under ice-cooling for 20 minutes. The precipitates were collected by filtration, washed with water, and dried to give 7-[2-(2-formamidothiazol-4-yl)-2-carbamoylmethoxyiminoacetamido]-3-cephem-4-carboxylic acid (syn isomer, 0.92 g.).

I.R. $\nu_{max}^{Nujol}$: 3420, 3230 (shoulder), 3050, 1760, 1700 (shoulder), 1630 cm$^{-1}$.

N.M.R. δ(DMSO-d$_6$, ppm): 3.63 (2H, d, J=3 Hz), 4.52 (2H, s), 5.17 (1H, s, J=5 Hz), 5.95 (1H, d, d, J=5 Hz, 8 Hz), 6.53 (1H, broad s), 7.18 (1H, s), 7.49 (1H, s), 7.53 (1H, s), 8.57 (1H, s), 9.91 (1H, d, J=8 Hz), 12.40 (1H, broad s).

EXAMPLE 10

(1) 2-(2-Formamidothiazol-4-yl)-2-(2-methylthiazol-4-yl-methoxyimino)acetic acid (syn isomer, 0.50 g.), N,N-dimethylformamide (0.123 g.), phosphoryl chloride (0.259 g.) and ethylacetate (6 ml.) were treated in a similar manner to that of Example 1-(1) to give an activated acid solution. The solution and a solution of 7-amino-3-cephem-4-carboxylic acid (0.306 g.), trimethylsilylacetamide (1.03 g.), and bis(trimethylsilyl)acetamide (0.90 ml.) in methyl acetate (3 ml.) were treated in a similar manner to that of Example 1-(1). Water (10 ml.) was added to the resultant mixture, and the ethyl acetate layer was separated, washed with a saturated aqueous solution of sodium chloride, dried over magnesium sulfate and then evaporated in vacuo to give 7-[2-(2-formamidothiazol-4-yl)-2-(2-methylthiazol-4-yl methoxyimino)acetamido]-3-cephem-4-carboxylic acid (syn isomer, 0.48 g.)

I.R. $\nu_{max}^{Nujol}$: 3170, 1770, 1680, 1650 cm$^{-1}$.

N.M.R. δ (DMSO-d$_6$, ppm): 2.62 (3H, s), 3.53 (2H, AB-q, J=18 Hz), 5.10 (1H, d, J=5 Hz), 5.21 (2H, s), 5.85 (1H, dd, J=8 Hz, 5 Hz), 6.45 (1H, t, J=3 Hz), 741 (2H, s), 8.60 (1H, s), 9.75 (1H, d, J=8 Hz).

(2) A mixture of 7-[2-(2-formamidothiazol-4-yl)-2-(2-methylthiazol-4-ylmethoxyimino)acetamido]-3-cephem-4-carboxylic acid (syn isomer, 240 mg.) and conc. hydrochloric acid (71 mg.) in methanol (2.5 ml.) was stirred at room temperature for 6.5 hours. After removing the solvent from the resultant solution in vacuo, the residue was triturated with diisopropyl ether. The precipitates were collected by filtration and washed with diisopropyl ether to give colorless crystals of 7-[2-(2-aminothiazol-4-yl)-2-(2-methylthiazol-4-ylmethoxyimino)acetamido]-3-cephem-4-carboxylic acid hydrochloride (syn isomer, 236 mg.)

I.R. $\nu_{max}^{Nujol}$: 1780, 1735, 1670, 1650, 1635 cm$^{-1}$.

N.M.R. δ (DMSO-d$_6$, ppm): 2.70 (3H, s), 3.62 (2H, m), 5.35 (1H, d), 5.42 (2H, s), 5.95 (1H, dd, J=8 Hz, 5 Hz), 6.48 (1H, t, J=3 Hz), 6.98 (1H, s), 7.70 (1H, s), 7.92 (1H, d, J=8 Hz).

EXAMPLE 11

(1) Vilsueier reagent was prepared from N,N-dimethylformamide (0.4 g.) and phosphoryl chloride (0.85 g.) in an usual manner. 2-(2-Formamidothiazol-4-yl)-2-(3-tert-butoxycarbonylaminopropoxyimino)acetic acid (syn isomer, 1.9 g.) was added to the suspension of the Vilsmeier reagent in ethyl acetate (20 ml.) under ice-cooling and stirred at the same temperature for 30 minutes [hereinafter referred to solution A].

Trimethylsilylacetamide (4.0 g.) was added to a stirred suspension of 4-nitrobenzyl 7-amino-3-chloro-3-cephem-4-carboxylate hydrochloride (2.0 g.) in ethyl acetate (30 ml.) and the mixture was stirred at 40° C. for 20 minutes. To the solution was added the above solution A all at once at −30° C. and stirred at −10° to −30° C. for an hour. Water and ethyl acetate (100 ml.) were added to the reaction mixture at −10° C. The ethyl acetate layer was separated, washed with a sodium bicarbonate saturated aqueous solution and a sodium chloride saturated aqueous solution subsequently. The solution was dried over magnesium sulfate and concentrated in vacuo. The residue was pulverized with diethyl ether to give 4-nitrobenzyl 7-[2-(2-formamidothiazol-4-yl)-2-(3-tert-butoxycarbonylaminopropoxyimino)acetamido]-3-chloro-3-cephem-4-carboxylate (syn isomer, 1.95 g.).

I.R. $\nu_{max}^{Nujol}$: 3430, 3350, 3250, 1780, 1730, 1710, 1660, 1605, 1520 cm$^{-1}$.

(2) A suspension of 4-nitrobenzyl 7-[2-(2-formamidothiazol-4-yl)-2-(3-tert-butoxycarbonylaminopropoxyimino)acetamido]-3-chloro-3-cephem-4-carboxylate (syn isomer, 1.9 g.), palladium-carbon (0.9 g.), methanol (20 ml.) and tetrahydrofuran (20 ml.) was subjected to catalytic reduction under ordinary pressure at room temperature for 6 hours. After the insoluble substance was removed by filtration and washed with methanol, the filtrate was concentrated in vacuo. The residue was dissolved in a mixture of ethyl acetate and a sodium bicarbonate aqueous solution, and filtered out. The ethyl acetate layer was separated and extracted with a sodium bicarbonate aqueous solution. The aqueous solution was washed with ethyl acetate and ethyl acetate was added thereto. The mixture was adjusted to pH 2.5 with 10% hydrochloric acid under ice-cooling. The ethyl acetate layer was washed with a sodium chloride saturated aqueous solution, dried over magnesium sulfate and evaporated in vacuo. The residue was pulverized with diisopropyl ether to give 7-[2-(2-formamidothiazol-4-yl)-2-(3-tert-butoxycarbonylaminopropoxyimino)acetamido]-3-chloro-3-cephem-4-carboxylic acid (syn isomer, 0.7 g.).

I.R. $\nu_{max}^{Nujol}$: 3200, 1780, 1690, 1660, 1540 cm$^{-1}$.

N.M.R. δ (DMSO-d$_6$, ppm): 1.43 (9H, s), 1.83 (2H, t, J=6 Hz), 3.08 (2H, m), 3.70 (2H, q, J=18 Hz), 4.15 (2H, t, J=6 Hz), 5.3 (1H, d, J=5 Hz), 5.90 (1H, dd, J=5 Hz, 8 Hz), 7.45 (1H, s), 8.57 (1H, s), 9.73 (1H, d, J=8 Hz), 12.7 (1H, broad s).

(3) Conc. hydrochloric acid (0.4 ml.) was added to the solution of 7-[2-(2-formamidothiazol-4-yl)-2-(3-tert-butoxycarbonylaminopropoxyimino)acetamido]-3-chloro-3-cephem-4-carboxylic acid (syn isomer, 0.6 g.) in methanil (20 ml.), and stirred at room temperature for 1.5 hours. After evaporating the solvent from the resultant mixture in vacuo, methanol was added to the residue. The mixture was evaporated in vacuo. The residue was dried over phosphorous pentoxide in vacuo to give 7-[2-(2-aminothiazol-4-yl)-2-(3-aminopropoxyimino)acetamido]-3-chloro-3-cephem-4-carboxylic acid dihydrochloride (syn isomer, 0.5 g.).

I.R. $\nu_{max}^{Nujol}$: 3400–3100, 1770, 1720 (sh), 1665, 1620, 1540 cm$^{-1}$.

N.M.R. δ(DMSO-d$_6$, ppm): 2.05 (2H, m), 2.90 (2H, m), 3.88 (2H, q, J=18 Hz), 4.25 (2H, m), 5.27 (1H, d, J=5Hz), 5.77 (1H, dd, J=5 Hz, 8 Hz), 6.92 (1H, s), 9.72 (1H, d, J=8 Hz).

EXAMPLE 12

(1) 2-(2-Formamidothiazol-4-yl)-2-(2-tert-butoxycarbonylaminoethoxyimino)acetic acid (syn isomer, 2 g.), N,N-dimethylformamide (0.45 g.), phosphoryl chloride (1.03 g.), trimethylsilylacetamide (5.9 g.), 4-nitrobenzyl 7-amino-3-chloro-3-cephem-4-carboxylate hydrochloride (2.3 g.) and ethyl acetate (60 ml.) were treated in a similar manner to that of Example 11-(1) to give 4-nitrobenzyl 7-[2-(2-formamidothiazol-4-yl)-2-(2-tert-butoxycarbonylaminoethoxyimino)acetamido]-3-chloro-3-cephem-4-carboxylate (syn isomer, 3.55 g.)

I.R. $\nu_{max}^{Nujol}$: 3300, 3200, 1780, 1730, 1680, 1610, 1520 cm$^{-1}$.

N.M.R. δ(DMSO-d$_6$, ppm): 1.32 (9H, s), 3.17 (2H, m), 4.33–3.70 (4H, m), 5.37 (1H, d, J=5 Hz), 5.47 (2H, s), 6.0 (1H, dd, J=8 Hz, 5 Hz), 7.47 (1H, s), 7.73 (2H, d, J=9 Hz), 8.30 (2H, d, J=9 Hz), 8.58 (1H, s), 9.87 (1H, d, J=8 Hz).

(2) 4-Nitrobenzyl 7-[2-(2-formamidothiazol-4-yl)-2-(2-tert-butoxycarbonylaminoethoxyimino)acetamido]-3-chloro-3-cephem-4-carboxylate (syn isomer, 3.3 g.), 10% palladium-carbon (1.7 g.), methanol (65 ml.) and tetrahydrofuran (65 ml.) were treated in similar manner to that of Example 11-(2) to give 7-[2-(2-formamidothiazol-4-yl)-2-(2-tert-butoxycarbonylaminoethoxyimino)acetamido]-3-chloro-3-cephem-4-carboxylic acid (syn isomer, 1.45 g.).

I.R. $\nu_{max}^{Nujol}$: 3400, 3200, 1780, 1670, 1535 cm$^{-1}$.

N.M.R. δ(DMSO-d$_6$, ppm): 1.37 (9H, s), 3.30 (2H, m), 3.77 (2H, q, J=17 Hz), 4.05 (2H, t, J=6 Hz), 5.25 (1H, d, J=5 Hz), 5.83 (1H, dd, J=8 Hz, 5 Hz), 7.37 (1H, s), 8.45 (1H, s), 9.53 (1H, d, J=8 Hz), 12.67 (1H, broad s).

(3) 7-[2-(2-Formamidothiazol-4-yl)-2-(2-tert-butoxycarbonylaminoethoxyimino)acetamido]-3-chloro-3-cephem-4-carboxylic acid (syn isomer, 1.3 g.), conc.hydrochloric acid (1.2 g.) and methanol (20 ml.) were treated in similar manner to that of Example 11-(3) to give 7-[2-(2-aminothiazol-4-yl)-2-(2-aminoethoxyimino)acetamido]-3-chloro-3-cephem-4-carboxylic acid dihydrochloride (syn isomer, 1.1 g.).

I.R. $\nu_{max}^{Nujol}$: 3350–3100, 1770, 1720, 1670, 1620, 1570, 1540 cm$^{-1}$.

N.M.R. δ(DMSO-d$_6$, ppm): 3.30 (2H, m), 3.87 (2H, q, J=17 Hz), 4.38 (2H, m), 5.25 (1H, d, J=5 Hz), 5.57 (1H, dd, J=8 Hz. 5 Hz), 7.0 (1H, s), 9.92 (1H, d, J=8 Hz).

EXAMPLE 13

(1) Vilsmeier reagent was prepared from N,N-dimethylformamide (0.6 g.) and phosphoryl chloride (1.2 g.) in an usual manner. 2-(2-Formamidothiazol-4-yl)-2-(3-tert-butoxycarbonylaminopropoxyimino)acetic acid (syn isomer, 2.6 g.) was added to a stirred suspension of the Vilsmeier reagent in ethyl acetate (30 ml.) under ice-cooling and stirred at the same temperature for 30 minutes [hereinafter referred to solution A].

Trimethylsilylacetamide (5.5 g.) was added to a stirred suspension of 7-amino-3-cephem-4-carboxylic acid (1.4 g.) in ethyl acetate (20 ml.), and the mixture was stirred at 40° C. for 30 minutes. The solution A was added to the solution at −10° to −30° C. and stirred at the same temperature for an hour. Water and ethyl acetate (100 ml.) were added to the reaction mixture at −10° C. and the ethyl acetate layer was separated. Water was added to the ethyl acetate layer, and adjusted to pH 7.5 with a sodium bicarbonate saturated aqueous solution. The aqueous solution was separated and ethyl acetate was added thereto. The mixture was adjusted to pH 2.8 with 10% hydrochloric acid under ice-cooling. The ethyl acetate layer was separated, washed with a sodium chloride saturated aqueous solution and dried over magnesium sulfate. The solution was concentrated in vacuo, and the residue was pulverized with diisopropyl ether to give 7-[2-(2-formamidothiazol-4-yl)-2-(3-tert-butoxycarbonylaminopropoxyimino)acetamido]-3-cephem-4-carboxylic acid (syn isomer, 2.2 g.)

I.R. $\nu_{max}^{Nujol}$: 3400–3150, 1780, 1680, 1660, 1540 cm$^{-1}$.

N.M.R. δ(DMSO-d$_6$, ppm): 1.43 (9H, s), 1.83 (2H, m), 3.03 (2H, broad s), 4.17 (2H, t, J=6 Hz), 5.17 (1H, d, J=5 Hz), 5.92 (1H, dd, J=5 Hz, 8 Hz), 6.53 (1H, m), 7.45 (1H, s), 8.57 (1H, s), 9.65 (1H, d, J=8 Hz), 12.7 (1H, broad s).

(2) Conc.hydrochloric acid (1.6 ml.) was added to a solution of 7-[2-(2-formamidothiazol-4-yl)-2-(3-tert-butoxycarbonylaminopropoxyimino)acetamido]-3-cephem-4-carboxylic acid (syn isomer, 2.1 g.) in methanol (30 ml.), and stirred at room temperature for 3.5 hours. After evaporating the solvent in vacuo, methanol was added to the residue and the mixture was evaporated in vacuo again. The residue was dissolved in water (30 ml.) and adjusted to pH 3.5 with a sodium bicarbonate saturated aqueous solution under ice-cooling. The solution was subjected to column chromatography on macroporous non-ionic adsorption resin "Diaion HP-20" (trademark, manufactured by Mitsubishi Chemical Industries Ltd.) and eluted with 30% aqueous isopropyl alcohol. The eluate was concentrated in vacuo and lyophilized to give 7-[2-(2-aminothiazol-4-yl)-2-(3-aminopropoxyimino)-acetamido]-3-cephem-4-carboxylic acid (syn isomer, 1.0 g.).

I.R. $\nu_{max}^{Nujol}$: 3400–3100, 1770, 1670–1580, 1520 cm$^{-1}$.

N.M.R. $\delta$(DMSO-d$_6$, ppm): 1.97 (2H, m), 2.92 (2H, m), 3.67 (2H, m), 4.17 (2H, m), 4.97 (1H, d, J=5 Hz), 5.72 (1H, m), 6.07 (1H, m), 6.77 (1H, s).

EXAMPLE 14

(1) Vilsmeier reagent was prepared from N,N-dimethylformamide (0.44 g.) and phosphoryl chloride (0.92 g.) in an usual manner. 2-(2-Formamidothiazol-4-yl)-2-(4-bromo-3-hydroxybenzyloxyimino)acetic acid (syn isomer, 2.0 g.) was added to the stirred suspension of Vilsmeier reagent in ethyl acetate (18 ml.) under ice-cooling, and stirred at the same temperature for 30 minutes to give a solution [hereinafter referred to solution A].

Trimethylsilylacetamide (3.9 g.) was added to a stirred suspension of 7-amino-3-cephem-4-carboxylic acid (1.0 g.) in ethyl acetate (10 ml.) and the mixture was stirred at 40° C. for 30 minutes.

To the solution was added the solution A all at once at −30° C., and stirred at −10° to −20° C. for an hour. Water (100 ml.) and ethyl acetate (100 ml.) were added to the resultant mixture at −10° C. After separating the organic layer, water (100 ml.) was added to the organic layer and adjusted to pH 7.0 with a sodium bicarbonate saturated solution. The aqueous layer was separated, and ethyl acetate was added thereto. The mixture was adjusted to pH 3.0 with 10% hydrochloric acid under ice-cooling. The organic layer was separated, washed with a sodium chloride saturated solution and dried over magnesium sulfate. The solution was concentrated in vacuo to give 7-[2-(2-formamidothiazol-4-yl)-2-(4-bromo-3-hydroxybenzyloxyimino)acetamido]-3-cephem-4-carboxylic acid (syn isomer, 2.0 g.).

I.R. $\nu_{max}^{Nujol}$: 3100–3400, 1780, 1670, 1550 cm$^{-1}$.

N.M.R. $\delta$ (DMSO-d$_6$, ppm): 3.77–3.40 (2H, m), 5.27–5.0 (3H, m), 5.88 (1H, dd, J=5 Hz, 8 Hz), 6.5 (1H, m), 6.83 (1H, dd, J=2 Hz, 8 Hz), 6.98 (1H, d, J=2 Hz), 7.43 (1H, s), 7.48 (1H, d, J=8 Hz), 8.57 (1H, s), 9.78 (1H, d, J=8 Hz), 10.3 (1H, broad s), 12.7 (1H, broad s).

(2) A mixture of 7-[2-(2-formamidothiazol-4-yl)-2-(4-bromo-3-hydroxybenzyloxyimino)acetamido]-3-cephem-4-carboxylic acid (syn isomer, 2.0 g.), conc. hydrochloric acid (1.1 g.), methanol (16 ml.) and tetrahydrofuran (10 ml.) was stirred at room temperature for 2 hours. After methanol was removed in vacuo, the residue was dissolved in a sodium bicarbonate aqueous solution and adjusted to pH 3.0 with 10% hydrochloric acid. The precipitates were collected by filtration, washed with water and dried over phosphorous pentoxide to give 7-[2-(2-aminothiazol-4-yl)-2-(4-bromo-3-hydroxybenzyloxyimino)-acetamido]-3-cephem-4-carboxylic acid (syn isomer, 1.6 g.).

I.R. $\nu_{max}^{Nujol}$: 3100–3400, 1780, 1660, 1640, 1540 cm$^{-1}$.

N.M.R. $\delta$ (DMSO-d$_6$, ppm): 3.58 (2H, m), 5.05 (2H, s), 5.1 (1H, d, J=5 Hz), 5.83 (1H, dd, J=5 Hz, 8 Hz), 6.48 (1H, m), 6.8 (1H, dd, J=2 Hz, 8 Hz), 6.83 (1H, s), 7.07 (1H, d, J=2 Hz), 7.43 (1H, d, J=8 Hz), 9.77 (1H, d, J=8 Hz).

EXAMPLE 15

(1) 2-(2-Formamidothiazol-4-yl)-2-(4-tert-butoxycarbonylaminomethylbenzyloxyimino)acetic acid (syn isomer, 1.4 g.), N,N-dimethylformamide (0.29 g.), phosphoryl chloride (0.6 g.), 7-amino-3-cephem-4-carboxylic acid (0.65 g.), trimethylsilylacetamide (2.5 g.) and ethyl acetate (18 ml.) were treated in a similar manner to that of Example 11-(1) to give 7-[2-(2-formamidothiazol-4-yl)-2-(4-tert-butoxycarbonylaminomethylbenzyloxyimino)acetamido]-3-cephem-4-carboxylic acid (syn isomer, 1.4 g.).

I.R. $\nu_{max}^{Nujol}$: 3150–3400, 1780, 1680, 1640(sh), 1540 cm$^{-1}$.

N.M.R. $\delta$ (DMSO-d$_6$, ppm): 1.42 (9H, s), 3.62 (2H, m), 4.12 (2H, d, J=6 Hz), 5.15 (1H, d, J=5 Hz), 5.2 (2H, s), 5.92 (1H, dd, J=5 Hz, 8 Hz), 6.52 (1H, m), 7.33 (4H, m), 7.43 (1H, s), 8.57 (1H, s), 9.8 (1H, d, J=8 Hz), 12.7 (1H, broad s).

(2) 7-[2-(2-Formamidothiazol-4-yl)-2-(4-tert-butoxycarbonylaminomethylbenzyloxyimino)acetamido]-3-cephem-4-carboxylic acid (syn isomer, 1.4 g.), conc. hydrochloric acid (0.95 g.) and methanol (15 ml.) were treated in a similar manner to that of Example 4-(2) to give 7-[2-(2-aminothiazol-4-yl)-2-(4-aminomethyl benzyloxyimino)acetamido]-3-cephem-4-carboxylic acid dihydrochloride (syn isomer, 0.9 g.).

I.R. $\nu_{max}^{Nujol}$: 3200, 3050, 1770, 1720, 1660, 1630, 1550 cm$^{-1}$.

N.M.R. $\delta$ (DMSO-d$_6$, ppm): 3.63 (2H, broad s), 4.0 (2H, d, J=6 Hz), 5.12 (1H, d, J=5 Hz), 5.22 (2H, s), 5.82 (1H, dd, J=5 Hz, 8 Hz), 6.48 (1H, m), 6.9 (1H, s), 7.48 (4H, s), 9.8 (1H, d, J=8 Hz).

EXAMPLE 16

(1) A solution of 7-amino-3-cephem-4-carboxylic acid (1.0 g.) and trimethylsilylacetamide (3.8 g.) in ethyl acetate (10 ml.) and a solution of 2-[2-(2,2,2-trifluoroacetamidothiazol-4-yl)]-2-(2,4-dichlorobenzyloxyimino)acetic acid (syn isomer, 2.0 g.), phosphoryl chloride (0.9 g.) and N,N-dimethylformamide (0.43 g.) in ethyl acetate (16 ml.) were treated in a similar manner to that of Example 1-(1) to give 7-[2-[2-(2,2,2-trifluoroacetamido)thiazol-4-yl]-2-(2,4-dichlorobenzyloxyimino)acetamido]-3-cephem-4-carboxylic acid (syn isomer, 2.3 g.).

I.R. $\nu_{max}^{Nujol}$: 3100–3400, 1790, 1730, 1660, 1630, 1580, 1550 cm$^{-1}$.

N.M.R. $\delta$ (DMSO-d$_6$, ppm): 3.65 (2H, m), 5.17 (1H, d, J=5 Hz), 5.33 (2H, s), 5.95 (1H, dd, J=5 Hz, 8 Hz), 6.53 (1H, m), 7.95 (1H, s), 7.87–7.35 (3H, m), 9.92 (1H, d, J=8 Hz).

(2) 7-[2-[2-(2,2,2-trifluoroacetamido)thiazol-4-yl]-2-(2,4-dichlorobenzyloxyimino)acetamido]-3-cephem-4-carboxylic acid (syn isomer, 2.0 g.) and tetrahydrofuran (30 ml.) were added to a solution of sodium acetate (4.6 g.) in water (100 ml.), and then the mixture was stirred at room temperature for 5 days. Ethyl acetate and water were added to the reaction mixture, and the aqueous layer was separated.

Ethyl acetate and tetrahydrofuran were added to the aqueous solution and adjusted to pH 6.2 with 10% hydrochloric acid. The aqueous layer was separated and adjusted to pH 3.0 with 10% hydrochloric acid. The precipitates were collected by filtration, washed with water and dried to give 7-[2-(2-aminothiazol-4-yl)-2-(2,4-dichlorobenzyloxyimino)-acetamido]-3-cephem-4-carboxylic acid (syn isomer, 0.3 g.). m.p. 167° to 193° C. (dec.).

I.R. $\nu_{max}^{Nujol}$: 3100–3400, 1770, 1650, 1630, 1530 cm$^{-1}$.

N.M.R. δ (DMSO-d$_6$, ppm): 3.63 (2H, m), 5.15 (1H, d, J=5 Hz), 5.27 (2H, s), 5.9 (1H, dd, J=5 Hz, 8 Hz), 6.53 (1H, m), 6.87 (1H, s), 7.82–7.33 (3H, m), 9.8 (1H, d, J=8 Hz).

EXAMPLE 17

(1) A solution of 4-nitrobenzyl 7-amino-3-cephem-4-carboxylate (2.5 g.), bis(trimethylsilyl)acetamide (4.5 g.) and trimethylsilylacetamide (6.8 g.) in tetrahydrofuran (50 ml.) and a solution of 2-[2-(2,2,2-trifluoroacetamido)thiazole-4-yl]-2-(4-fluorobenzyloxyimino)acetic acid (syn isomer, 3.2 g.), phosphoryl chloride (15 g.) and N,N-dimethylformamide (0.7 g.) in ethyl acetate (32.8 ml.) were treated in a similar manner to that of Example 1-(1) to give 4-nitrobenzyl 7-[2-[2-(2,2,2-trifluoroacetamido)thiazol-4-yl]-2-(4-fluorobenzyloxyimino)acetamido]-3-cephem-4-carboxylate (syn isomer, 4.85 g.).

I.R. $\nu_{max}^{Nujol}$: 3200, 1780, 1720, 1650, 1600 cm$^{-1}$.

N.M.R. δ (DMSO-d$_6$, ppm): 3.66 (2H, m), 5.00–5.34 (3H, m), 5.44 (2H, s), 5.98 (1H, dd, J=5 Hz, 8 Hz), 6.69 (1H, m), 7.00–7.62 (4H, m), 7.56 (1H, s), 7.72 (2H, d, J=8 Hz), 8.24 (2H, d, J=8 Hz), 9.91 (1H, d, J=8 Hz).

(2) A mixture of 4-nitrobenzyl 7-[2-[2-(2,2,2-trifluoroacetamido)thiazol-4-yl]-2-(4-fluorobenzyloxyimino)acetamido]-3-cephem-4-carboxylate (syn isomer, 4.65 g.), 10% palladium carbon (2.3 g) in water (9.3 ml.), acetic acid (0.93 ml.), tetrahydrofuran (93 ml.) and methanol (93 ml.) were treated in a similar manner to that of Exaple 7-(2) to give 7-[2-[2-(2,2,2-trifluoroacetamido)thiazol-4-yl]-2-(4-fluorobenzyloxyimino)-acetamido]-3-cephem-4-carboxylic acid (syn isomer, 3.15 g.).

I.R. $\nu_{max}^{Nujol}$: 3250, 1780, 1730, 1660 cm$^{-1}$.

N.M.R. δ (DMSO-d$_6$, ppm): 3.57 (2H, m), 5.06–5.43 (3H, m), 5.91 (1H, dd, J=4 Hz, 8 Hz), 6.51 (1H, m), 7.01–7.75 (4H, m), 7.56 (1H, s), 9.85 (1H, d, J=8.0 Hz).

(3) A mixture of 7-[2-[2-(2,2,2-trifluoroacetamido)-thiazol-4-yl]-2-(4-fluorobenzyloxyimino)acetamido]-3-cephem-4-carboxylic acid (syn isomer, 2.9 g.), sodium acetate (4.1 g.), water (60 ml.) and tetrahydrofuran (30 ml.) was treated in a similar manner to that of Example 16-(2) to give 7-[2-(2-aminothiazol-4-yl)-2-(4-fluorobenzyloxyimino)acetamido]-3-cephem-4-carboxylic acid (syn isomer, 2.68 g.), m.p. 203° to 207° C. (dec.).

I.R. $\nu_{max}^{Nujol}$: 3200, 1770, 1660, 1600 cm$^{-1}$.

N.M.R. δ (DMSO-d$_6$, ppm): 3.64 (2H, m), 4.99–5.37 (3H, m), 5.87 (1H, dd, J=4 Hz, 8 Hz), 6.53 (1H, m), 6.78 (1H, s), 7.02–7.82 (4H, m), 9.73 (1H, d, J=8.0 Hz).

EXAMPLE 18

(1) A solution of 4-nitrobenzyl 7-amino-3-cephem-4-carboxylate (2.01 g.), trimethylsilylacetamide (5.51 g.) and tetrahydrofuran (40 ml.) and a solution of 2-[2-(2,2,2-trifluoroacetamido)thiazol-4-yl]-2-(4-methylbenzyloxyimino)acetic acid (syn isomer, 2.32 g.), phosphoryl chloride (1.20 g.) and N,N-dimethylformamide (570 mg.) in tetrahydrofuran (12 ml.) were treated in a similar manner to that of Example 1-(1) to give 4-nitrobenzyl 7-[2-[2-(2,2,2-trifluoroacetamido)thiazol-4-yl]-acetamido]-3-cephem-4-carboxylate (syn isomer, 4.43 g.).

I.R. $\nu_{max}^{Nujol}$: 1780, 1720, 1650, 1600, 1510, 1340, 1280, 1210, 1150 cm$^{-1}$.

N.M.R. δ (DMSO-d$_6$, ppm): 1.97 (3H, s), 3.60 (2H, m), 5.13 (2H, s), 5.17 (1H, d, J=6 Hz), 5.40 (2H, s), 5.92 (1H, dd, J=8 Hz, 6 Hz), 6.63 (1H, t, J=4 Hz), 7.17–7.37 (5H, m), 7.93 (4H, dd, J=23 Hz, 8 Hz), 9.75 (1H, d, J=8 Hz).

(2) A mixture of 4-nitrobenzyl 7-[2-[2-(2,2,2-trifluoroacetamido)thiadol-4-yl]-2-(4-methylbenzyloxyimino)-acetamido]-3-cephem-4-carboxylate (syn isomer, 4.43 g.), 10% palladium carbon (2.5 g.), methanol (80 ml.) and tetrahydrofuran (60 ml.) was treated in a similar manner to that of Example 7-(2) to give 7-[2-[2-(2,2,2-trifluoroacetamido)thiazol-4-yl]-2-(4-methylbenzyloxyimino)acetamido]-3-cephem-4-carboxylic acid (syn isomer, 4.5 g.).

I.R. $\nu_{max}^{Nujol}$: 1770, 1650, 1260, 1200, 1160, 1010 cm$^{-1}$.

N.M.R. δ (DMSO-d$_6$, ppm): 2.33 (3H, s), 3.63 (2H, m), 5.13 (1H, d, J=5 Hz), 5.17 (2H, s), 5.90 (1H, dd, J=8 Hz, 5 Hz), 6.50 (1H, t, J=5 Hz), 7.10–7.43 (4H, m), 7.50 (1H, s), 9.83 (1H, d, J=8 Hz).

(3) A mixture of 7-[2-[2-(2,2,2-trifluoroacetamido)-thiazol-4-yl]-2-(4-methylbenzyloxyimino)acetamido]-3-cephem-4-carboxylic acid (syn isomer, 4.5 g.), sodium acetate 3 hydrate (12.5 g.), water (250 ml.) and tetrahydrofuran (20 ml.) was treated in a similar manner to that of Example 16-(2) to give 7-[2-(2-aminothiazol-4-yl)-2-(4-methylbenzyloxyimino)acetamido]-3-cephem-4-carboxylic acid (syn isomer, 0.84 g.), m.p. 135°–155° C. (dec.).

I.R. $\nu_{max}^{Nujol}$: 1770, 1660–1630, 1530, 1450, 1370, 1010 cm$^{-1}$.

N.M.R. δ (DMSO-d$_6$, ppm): 2.27 (3H, s), 3.53 (2H, m), 5.03–5.10 (3H, m), 5.80 (1H, dd, J=8 Hz, 6 Hz), 6.43 (1H, t, J=3 Hz), 6.70 (1H, s), 7.20 (4H, dd, J=8 Hz, 11 Hz), 9.66 (1H, d, J=8 Hz).

What we claim is:

1. A compound of the formula:

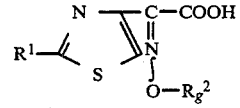

wherein R$^1$ is amino or protected amino, and R$^2_g$ is lower alkyl of from one to six carbon atoms substituted with a substituent selected from the group consisting of amino, lower alkoxycarboxamido, lower alkenylthio, substituted phenyl with, amino (lower) alkyl or amido (lower) alkyl substituent, heterocyclic selected from the group consisting of furyl, pyrrolyl, imidazolyl, pyrazolyl, pyridyl, picolyl, pyrimidinyl, pyrazinyl, pyridazinyl, triazolyl, tetrazolyl, oxazolyl, isoxazolyl, oxadiazolyl, thiazolyl, isothiazolyl and thiadiazolyl, and substituted heterocyclic with at least one lower alkyl, hydroxy or amino substituent, and its ester and a salt thereof.

2. The compound of claim 1 wherein the substituent on the lower alkyl of $R^2g$ is amino.

3. The compound of claim 1 wherein the substituent on the lower alkyl of $R^2g$ is lower alkoxycarboxamido.

4. The compound of claim 1 wherein the substituent on the lower alkyl of $R^2g$ is lower alkenylthio.

5. The compound of claim 1 wherein the substituent on the lower alkyl of $R^2g$ is phenyl substituted with amino (lower) alkyl.

6. The compound of claim 1 wherein the substituent on the lower alkyl of $R^2g$ is phenyl substituted with amido (lower) alkyl.

7. The compound of claim 1 wherein the substituent on the lower alkyl of $R^2g$ is heterocyclic selected from the group consisting of furyl, pyrrolyl, imidazolyl, pyrazolyl, pyridyl, picolyl, pyrimidinyl, pyrazinyl, pyridazinyl, triazolyl, tetrazolyl, oxazolyl, isoxazolyl, oxadiazolyl, thiazolyl, isothiazolyl and thiadiazolyl, and substituted heterocyclic with at least one lower alkyl, hydroxy or amino substituent.

* * * * *